United States Patent
Kim

(10) Patent No.: US 11,154,590 B2
(45) Date of Patent: *Oct. 26, 2021

(54) NKX3.2 FRAGMENT AND PHARMACEUTICAL COMPOSITION COMPRISING SAME AS ACTIVE INGREDIENT

(71) Applicant: ICM CO., LTD., Seoul (KR)

(72) Inventor: Dae-Won Kim, Seoul (KR)

(73) Assignee: ICM CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,370

(22) Filed: Feb. 28, 2020

(65) Prior Publication Data
US 2020/0188480 A1    Jun. 18, 2020

Related U.S. Application Data

(62) Division of application No. 16/348,540, filed as application No. PCT/KR2017/012651 on Nov. 9, 2017.

(30) Foreign Application Priority Data

Nov. 9, 2016 (KR) .................. 10-2016-0149090

(51) Int. Cl.
*A61K 38/17* (2006.01)
*A61P 19/02* (2006.01)

(52) U.S. Cl.
CPC ............... *A61K 38/17* (2013.01); *A61P 19/02* (2018.01)

(58) Field of Classification Search
CPC .... A61K 38/16; A61K 38/17; A61K 38/1703; A61K 38/1709
See application file for complete search history.

(56) References Cited

FOREIGN PATENT DOCUMENTS

| KR | 10-1150900 B1 | 5/2012 | | |
|---|---|---|---|---|
| WO | 2011093647 A2 | 8/2011 | | |
| WO | WO-2011093647 A2 | * 8/2011 | ......... | A61K 38/1709 |
| WO | 2012/097057 A2 | 7/2012 | | |
| WO | 2018194423 A1 | 10/2018 | | |

OTHER PUBLICATIONS

XP_011839517.1 homebox polypeptide sequence of Mandrillus leucophaeus, provided in Feb. 28, 20 IDS (Year: 2015).*
NCBI Reference Sequence: NP_001180.1, Oct. 5, 2016.
Marjolein M. J. Caron et al., "BAPX-1/NKX-3.2 Acts as a Chondrocyte Hypertrophy Molecular Switch in Osteoarthritis", Arthritis & Rheumatology, Nov. 2015, pp. 2944-2956, vol. 67, No. 11.
Jeong-Ah Kim et al., "Suppression of Nkx3.2 by phosphatidylinositol-3-kinase signaling regulates cartilage development by modulating chondrocyte hypertrophy", Cellular Signalling, 2015, pp. 2389-2400, vol. 27.
Minsun Park et al., "Constitutive RelA activation mediated by Nkx3.2 controls chondrocyte viability", Nature Cell Biology, Mar. 2007, pp. 287-298, vol. 9, No. 3.
NCBI Reference Sequence: XP_011839517.1, Mar. 30, 2015.
Communication issued in Korean Patent Application No. 10-2017-0148493 dated Jan. 28, 2019.
International Search Report of PCT/KR2017/012651 dated Aug. 3, 2018 [PCT/ISA/210].

* cited by examiner

*Primary Examiner* — Larry D Riggs, II
*Assistant Examiner* — Joseph Fischer
(74) *Attorney, Agent, or Firm* — Sughrue Mion, PLLC

(57) ABSTRACT

An Nkx3.2 fragment with improved stability under a histopathological environment of arthritis and a pharmaceutical composition containing the Nkx3.2 as an active ingredient are disclosed. The Nkx3.2 fragment has a function to activate NF-κB at the similar level to full-length Nkx3.2 and resistance to proteolysis by Siah1. In addition, the Nkx3.2 fragment exhibited at least a 10-fold improvement in degenerative arthritis treatment effect compared with Nkx3.2 in an animal model-based in vivo efficacy evaluation. Therefore, the Nkx3.2 fragment can be favorably used in the prevention or treatment of arthritis.

18 Claims, 5 Drawing Sheets

Specification includes a Sequence Listing.

[FIG. 1]
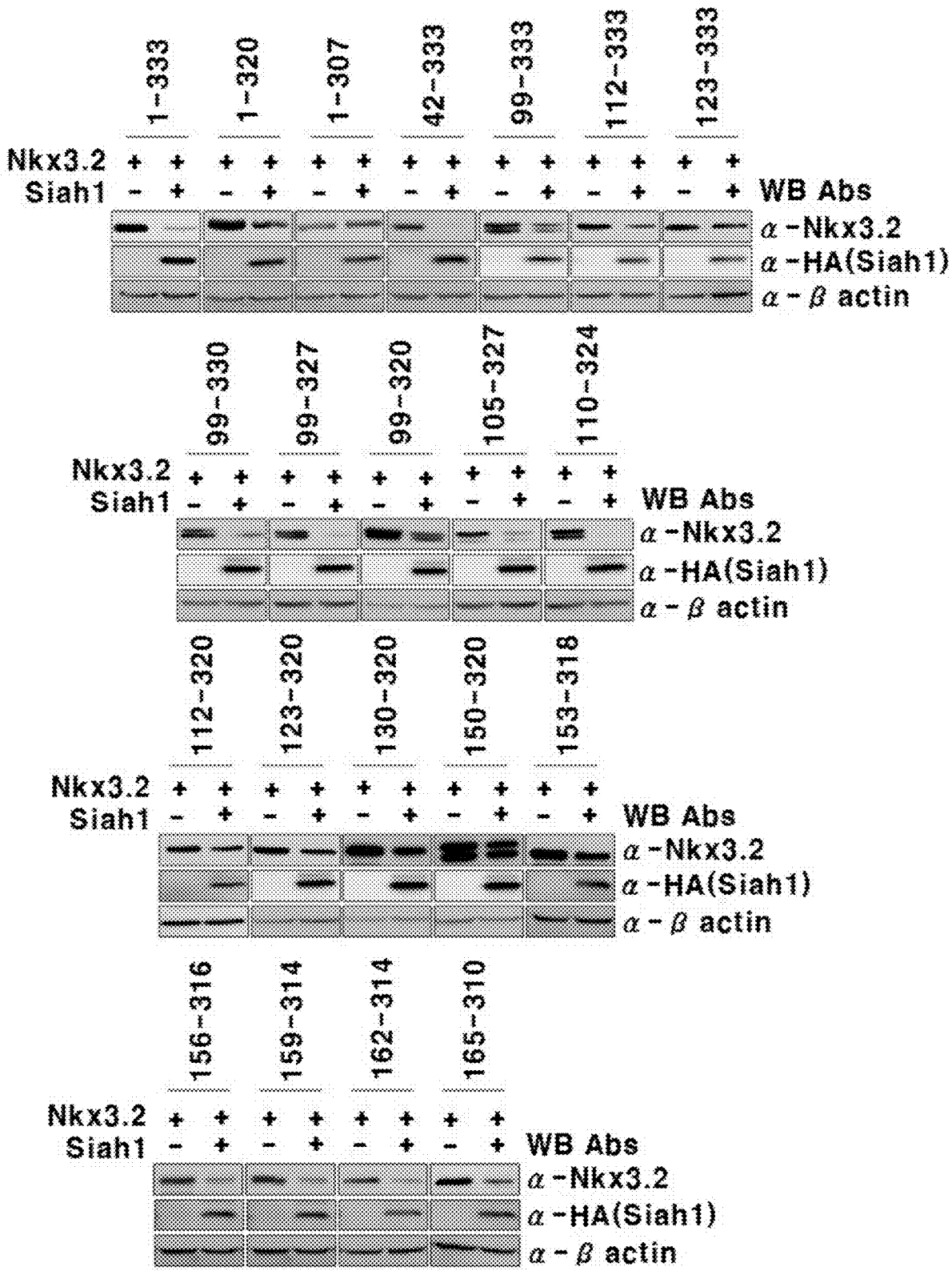

[FIG. 2]
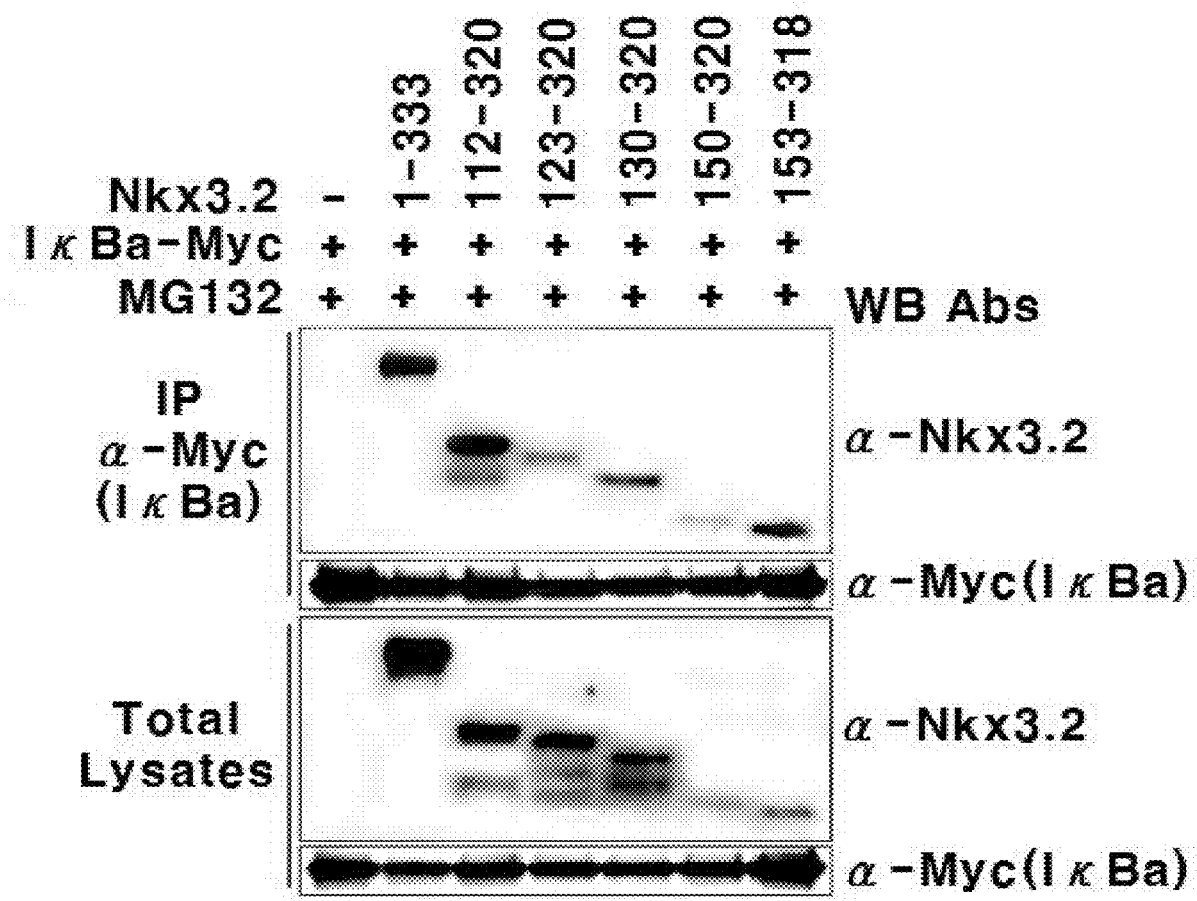

[FIG. 3]
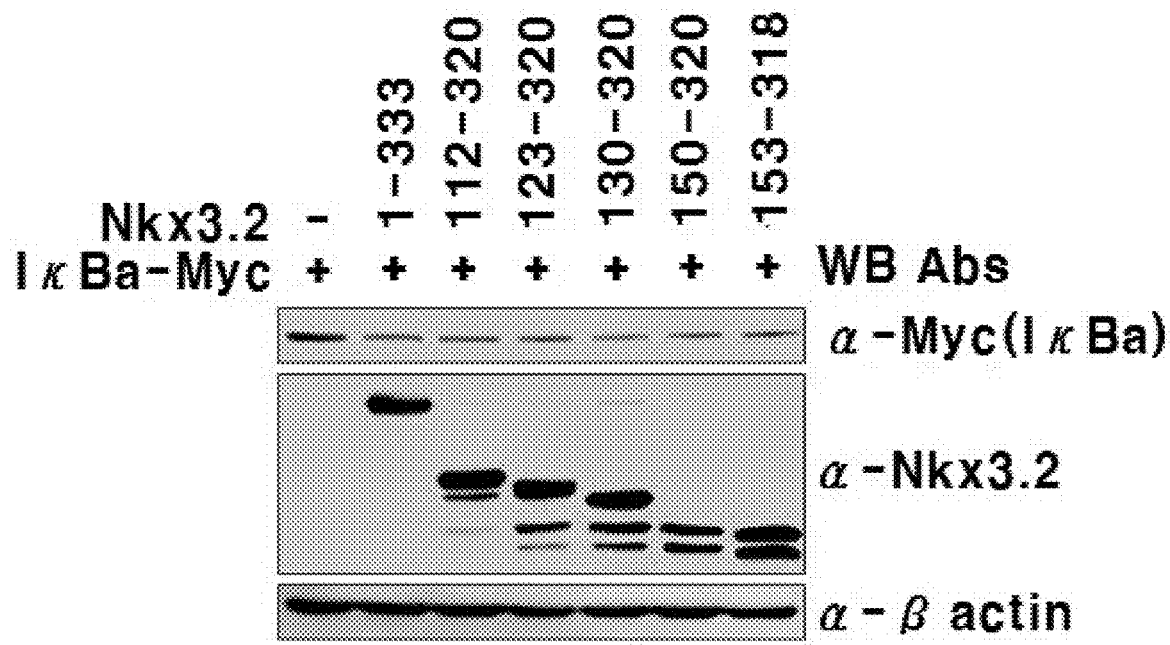
[FIG. 4]
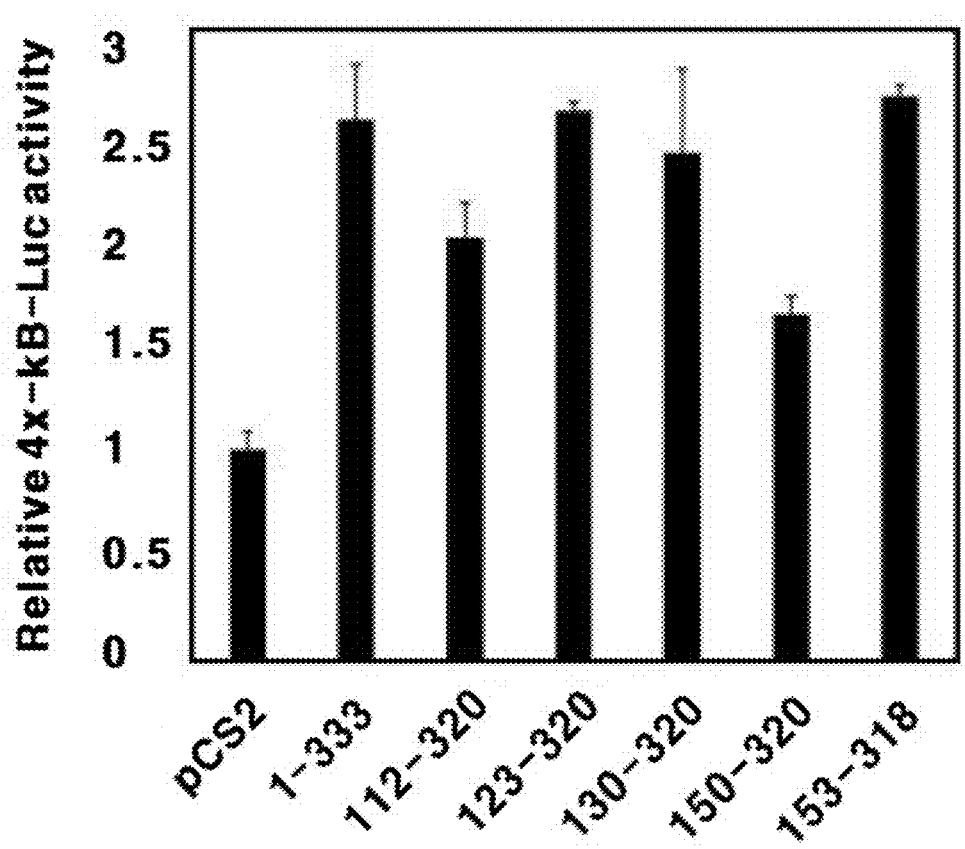

[FIG. 5]
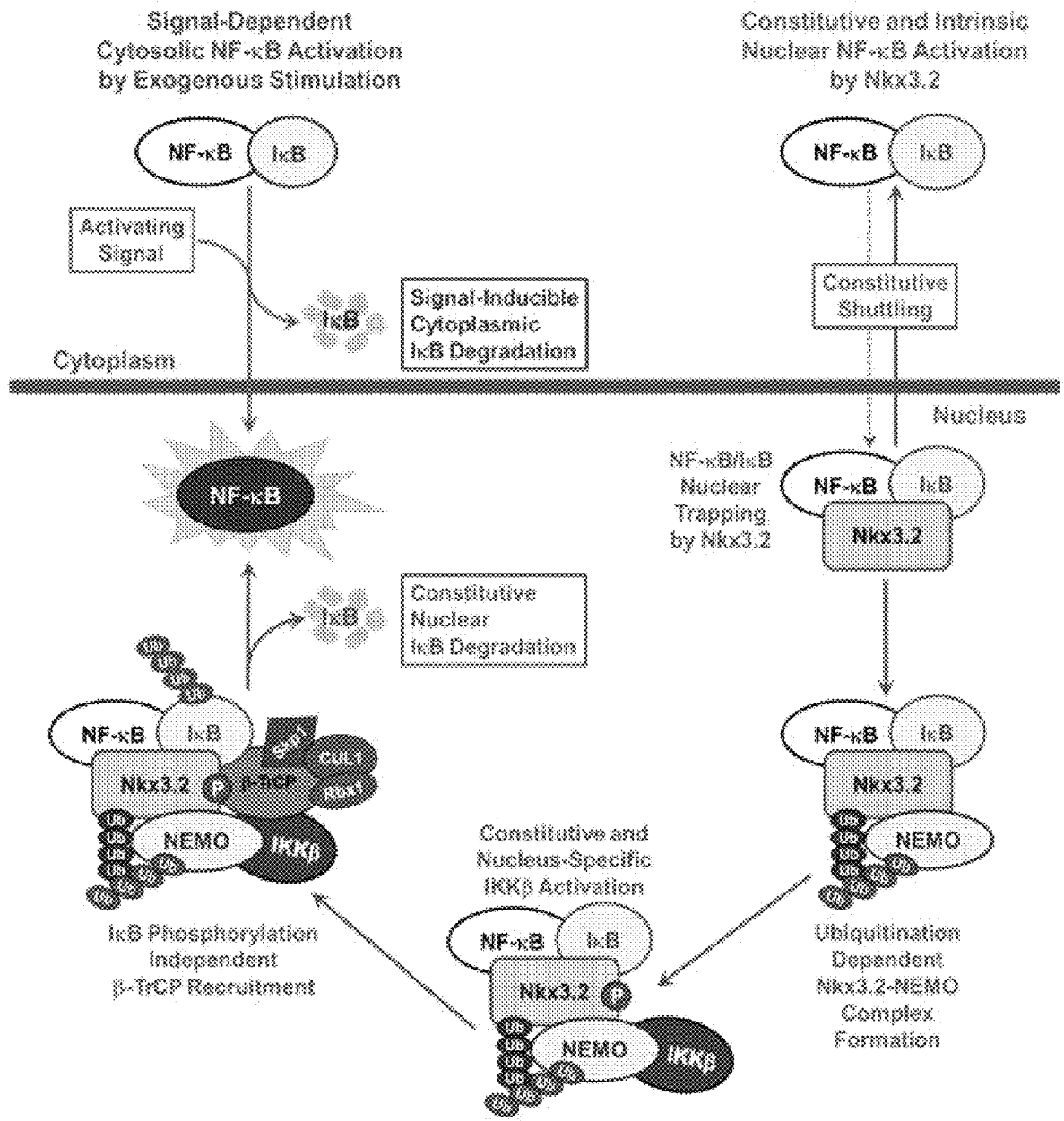
[FIG. 6]
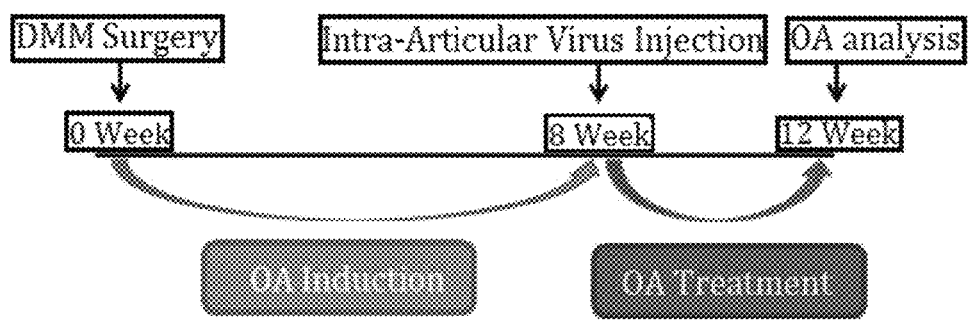

[FIG. 7]
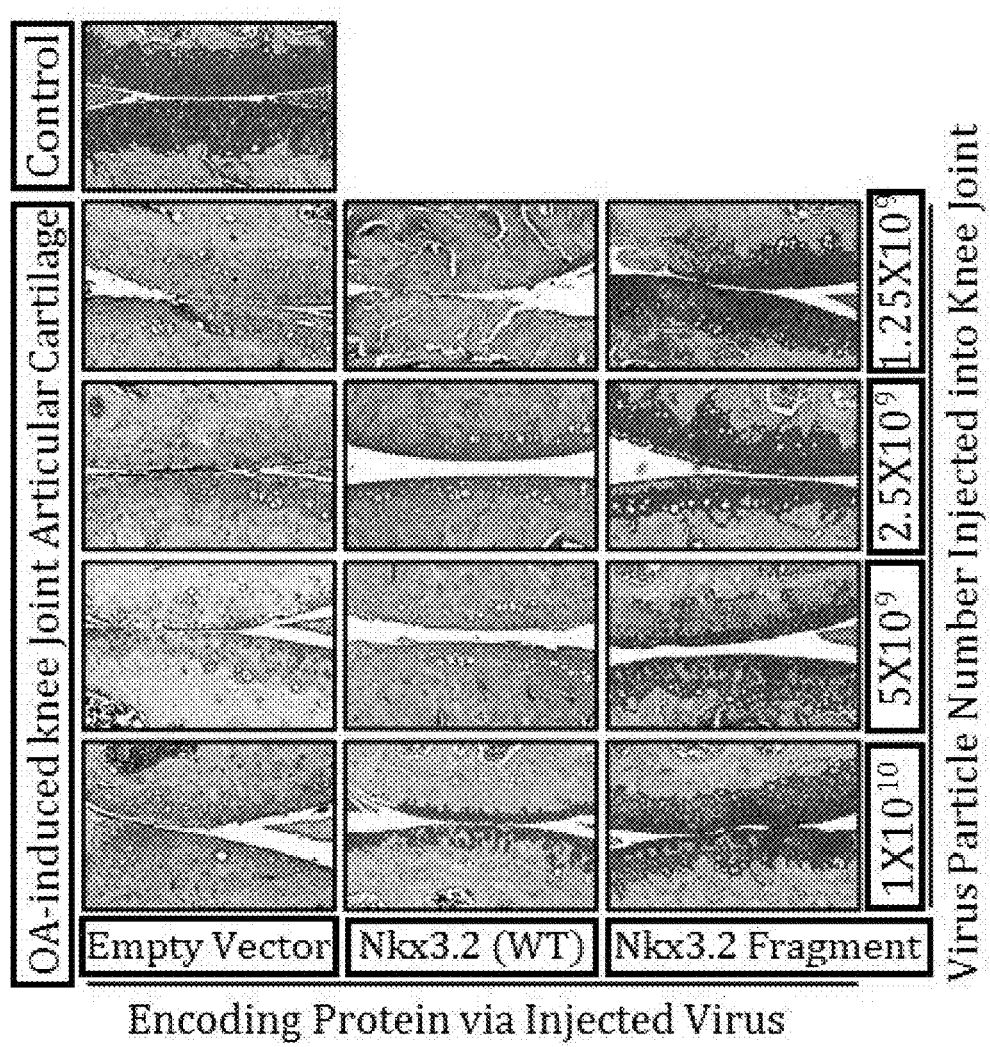
[FIG. 8]
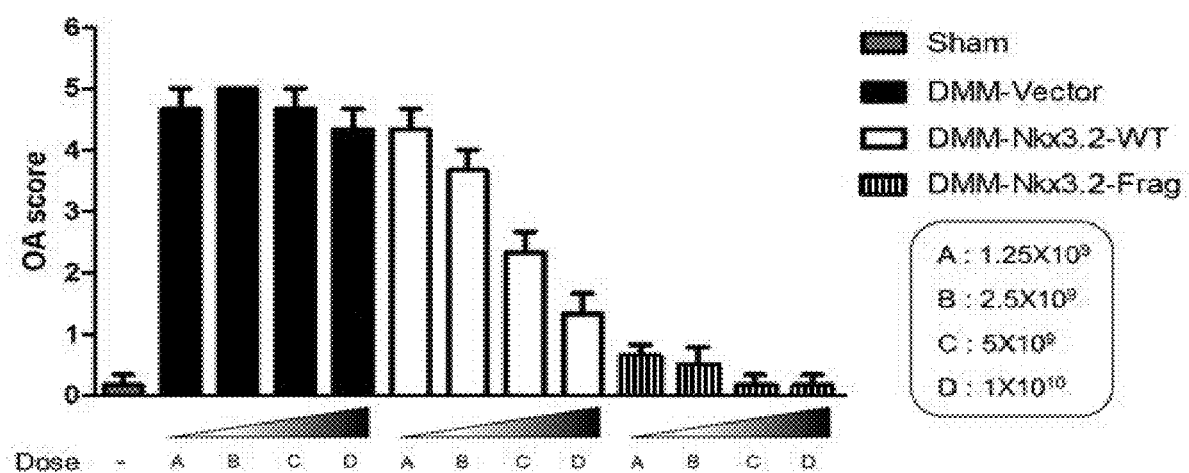

US 11,154,590 B2

NKX3.2 FRAGMENT AND PHARMACEUTICAL COMPOSITION COMPRISING SAME AS ACTIVE INGREDIENT

CROSS REFERENCE TO RELATED APPLICATIONS

This application is a Divisional Application of U.S. application Ser. No. 16/348,540, which is a National Stage of International Application No. PCT/KR2017/012651, filed Nov. 9, 2017, claiming priority to Korean Patent Application No. 10-2016-0149090, filed Nov. 9, 2016.

TECHNICAL FIELD

The present invention relates to an Nkx3.2 fragment with improved stability under a pathological tissue environment of arthritis, and a pharmaceutical composition comprising the same as an active ingredient.

BACKGROUND ART

Degenerative arthritis, which is one of the most commonly occurring arthritis, is a disease in which degenerative changes damage cartilage tissues that protect a joint, bones and ligaments that form a joint, and the like, thereby resulting in inflammation and pain. Conventionally, treatment of degenerative arthritis has been carried out primarily through control of inflammation. However, it has been proven that the control of inflammation cannot be a fundamental therapeutic technique.

Therefore, in order to treat the cause of degenerative arthritis, identification of a target that regulates processes, such as generation, differentiation, death, calcification, of chondrocytes and development of methods to control the target are required.

Meanwhile, overexpressed Nkx3.2 (NK3 homeobox 2) has been shown to suppress loss of cartilage tissue caused by degenerative arthritis, and thus the protein may be used for treatment of degenerative arthritis. In this regard, Korean Patent No. 10-1150900 describes a composition for treating arthritis, an arthritis diagnostic kit, or a method of screening a therapeutic agent for arthritis using Nkx3.2 protein.

In addition, it has been shown that degradation of Nkx3.2 protein is promoted by the Indian Hedgehog (Ihh) signaling, which is activated during the process of hypertrophy and calcification of chondrocytes, and this phenomenon is mediated by a proteolytic enzyme, Siah1. Furthermore, it has been shown that the Indian Hedgehog signaling increases with development of degenerative arthritis accompanied by chondrocyte calcification, and controlling the Indian Hedgehog signaling suppresses the progression of degenerative arthritis in animal models.

DETAILED DESCRIPTION OF THE INVENTION

Technical Problem

The present inventors conducted studies to develop therapeutics for degenerative arthritis using Nkx3.2 variants that can effectively function under the pathological environment of degenerative arthritis. Consequently, the present inventors produced Nkx3.2 fragments that are resistant to proteolysis induced by Siah1. The present inventors also identified that the aforementioned Nkx3.2 fragments can induce NF-κB activation at the level comparable to the full-length Nkx3.2. Furthermore, the present inventors found that the Nkx3.2 fragments exhibit remarkably improved therapeutic efficacy against degenerative arthritis as compared to the full-length Nkx3.2.

Solution to Problem

In order to achieve the above objects, the present invention provides a polypeptide represented by the following Formula (I):

N-terminal extension domain-core domain-C-terminal extension domain    (I), in the above Formula (I), the core domain is a polypeptide comprising the amino acid sequence of SEQ ID NO: 1;

the N-terminal extension domain is a polypeptide comprising the amino acid sequence of SEQ ID NO: 35 in which 1 to 53 amino acids are consecutively deletable from the N-terminus to the C-terminal direction, starting from the amino acid at position 1 of SEQ ID NO: 35; and the C-terminal extension domain is a polypeptide comprising the amino acid sequence of SEQ ID NO: 5 in which 1 to 23 amino acids are consecutively deletable from the C-terminus to the N-terminal direction, starting from the amino acid at position 24 of SEQ ID NO: 5.

The present invention also provides a polypeptide represented by the following Formula (II):

N-terminal extension domain-core domain-C-terminal extension domain    (II), in the above Formula (II), the core domain is a polypeptide comprising the amino acid sequence of SEQ ID NO: 37;

the N-terminal extension domain is a polypeptide comprising the amino acid sequence of SEQ ID NO: 39 in which 1 to 41 amino acids are consecutively deletable from the N-terminus to the C-terminal direction, starting from the amino acid at position 1 of SEQ ID NO: 39; and the C-terminal extension domain is a polypeptide comprising the amino acid sequence of SEQ ID NO: 41 in which 1 to 15 amino acids are consecutively deletable from the C-terminus to the N-terminal direction, starting from the amino acid at position 16 of SEQ ID NO: 41.

Furthermore, the present invention provides polynucleotides encoding the aforementioned polypeptides.

In addition, the present invention provides expression vectors comprising the aforementioned polynucleotides.

Furthermore, the present invention provides host cells harboring the aforementioned expression vectors.

In addition, the present invention provides pharmaceutical compositions for preventing or treating arthritis, comprising any of the aforementioned polypeptide as an active ingredient.

Furthermore, the present invention provides recombinant viruses comprising the aforementioned polynucleotides.

In addition, the present invention provides pharmaceutical compositions for preventing or treating arthritis, comprising any of the aforementioned recombinant virus as an active ingredient.

Furthermore, the present invention provides methods of preventing or treating arthritis, comprising the step of administering the aforementioned pharmaceutical compositions to a subject in need thereof.

Advantageous Effects of Invention

The Nkx3.2 fragments of the present invention have the function of activating NF-κB at the level comparable to the full-length Nkx3.2 and are resistant to proteolysis mediated by Siah1. In addition, the aforementioned Nkx3.2 fragments exhibit improved therapeutic effects against degenerative arthritis as compared with the full length Nkx3.2 in animal model-based in vivo efficacy evaluation. Thus, the Nkx3.2 fragments can be effectively used for preventing or treating arthritis.

BRIEF DESCRIPTION OF DRAWINGS

FIG. 1 is photographic illustration showing the resistance of Nkx3.2 fragments against proteolysis mediated by Siah1.

FIG. 2 is photographic illustration showing the binding of Nkx3.2 fragments to IκBα.

FIG. 3 is photographic illustration showing induction of degradation of IκBα by NKx3.2 fragments.

FIG. 4 is a graph showing activation of the transcriptional activity of NF-κB by NKx3.2 fragments.

FIG. 5 is a schematic diagram depicting the molecular mechanism underlying the NF-κB activation process induced by Nkx3.2.

FIG. 6 is a schematic diagram for the animal experiment procedure for evaluation of the therapeutic effect of Nkx3.2 fragments using a degenerative arthritis-induced animal model.

FIG. 7 is photographic illustration showing histopathological evaluation of the therapeutic efficacy against degenerative arthritis of Nkx3.2 or Nkx3.2 fragments expressed in the affected areas.

FIG. 8 is a graph showing the severity of degenerative arthritis on a scale of 0 to 5 based on quantitative evaluation of overall data obtained through histological analysis.

BEST MODE FOR CARRYING OUT THE INVENTION

Hereinafter, the present invention will be described in detail.

The present invention provides a polypeptide represented by the following Formula (I):

N-terminal extension domain-core domain-C-terminal extension domain     (I), in the above formula (I)

the core domain is a polypeptide comprising the amino acid sequence of SEQ ID NO: 1;

the N-terminal extension domain is a polypeptide comprising the amino acid sequence of SEQ ID NO: 35 in which 1 to 53 amino acids are consecutively deletable from the N-terminus to the C-terminal direction, starting from the amino acid at position 1 of SEQ ID NO: 35; and the C-terminal extension domain is a polypeptide comprising the amino acid sequence of SEQ ID NO: 5 in which 1 to 23 amino acids are consecutively deletable from the C-terminus to the N-terminal direction, starting from the amino acid at position 24 of SEQ ID NO: 5.

The core domain is a polypeptide comprising the amino acid sequence from position 166 to position 309 of the full-length Nkx3.2 protein. The full-length Nkx3.2 protein may include the amino acid sequence of SEQ ID NO: 7, and the core domain may include the amino acid sequence of SEQ ID NO: 1.

The N-terminal extension domain is a domain bound to the N-terminus of the above-mentioned core domain, and is a polypeptide comprising the amino acid sequence from position 112 to position 165 of the full-length Nkx3.2 protein. The N-terminal extension domain may include the amino acid sequence of SEQ ID NO: 35.

The N-terminal extension domain may be a polypeptide comprising the amino acid sequence of SEQ ID NO: 35, or a polypeptide comprising the amino acid sequence of SEQ ID NO: 35 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acid residues are deleted from the N-terminus to C-terminal direction, starting from the amino acid at position 1 of SEQ ID NO: 35. In some embodiments of the present invention, the N-terminal extension domain may be a polypeptide comprising the amino acid sequence of SEQ ID NO: 35, or a polypeptide comprising the amino acid sequence of SEQ ID NO: 35 in which 11, 18, 38, 41, 44, 47, 50, or 53 amino acid residues are deleted from the N-terminus to the C-terminal direction, starting from the amino acid at position 1 of SEQ ID NO: 35.

The C-terminal extension domain is a domain bound to the C-terminus of the above-mentioned core domain, and is a polypeptide comprising the amino acid sequence from positions 310 to 333 of the full-length Nkx3.2 protein. The C-terminal extension domain may include the amino acid sequence of SEQ ID NO: 5.

The C-terminal extension domain may be a polypeptide comprising the amino acid sequence of SEQ ID NO: 5, or a polypeptide comprising the amino acid sequence of SEQ ID NO: 5 in which 1, 2, 3, 4, 5, 6, 7, 8, 9, 10, 11, 12, 13, 14, 15, 16, 17, 18, 19, 20, 21, 22, or 23 amino acid residues are deleted from the C-terminus to the N-terminal direction, starting from the amino acid at position 24 of SEQ ID NO: 5.

Specifically, the C-terminal extension domain may be a polypeptide comprising the amino acid sequence of SEQ ID NO: 5, or a polypeptide comprising the amino acid sequence of SEQ ID NO: 5 in which 13, 14, 15, 16, 17, 18, 19, 20, 21, 22, or 23 amino acid residues are deleted from the C-terminus to the N-terminal direction, starting from the amino acid at position 24 of SEQ ID NO: 5.

In some embodiments of the present invention, the C-terminal extension domain may be a polypeptide comprising the amino acid sequence of SEQ ID NO: 5, or a polypeptide comprising the amino acid sequence of SEQ ID NO: 5 in which 13, 15, 17, 19, 21, or 23 amino acid residues are deleted from the C-terminus to the N-terminal direction, starting from the amino acid at position 24 of SEQ ID NO: 5.

Deletion of the amino acid residues may occur in either or both of the N-terminal extension domain and the C-terminal extension domain. In certain embodiments, the polypeptide may include the amino acid sequence of SEQ ID NO: 13, 14, 20, 21, 22, 23, 24, 25, 26, 27, or 28.

The present invention provides a polypeptide comprising the amino acid sequence of SEQ ID NO: 13 or a fragment thereof. The fragment may be a polypeptide comprising the amino acid sequence of SEQ ID NO: 13 in which 1 to 53 amino acids are consecutively deleted from the N-terminus to the C-terminal direction, starting from the amino acid at position 1 of SEQ ID NO: 13. In addition, the fragment may be a polypeptide comprising the amino acid sequence of SEQ ID NO: 13 in which 1 to 23 amino acids are consecutively deleted from the C-terminus to the N-terminal direction, starting from the amino acid at position 333 of SEQ ID NO: 13.

In other embodiments of the present invention, the polypeptide may include the amino acid sequence of SEQ ID NO: 13. In addition, the polypeptide may be a polypeptide comprising the amino acid sequence of SEQ ID NO: 13 in which 11, 18, 38, 41, 44, 47, 50, or 53 amino acid residues are deleted from the N-terminus to the C-terminal direction, starting from the amino acid at position 1 of SEQ ID NO: 13. In addition, the polypeptide may be a polypeptide comprising the amino acid sequence of SEQ ID NO: 13 in which 13, 15, 17, 19, 21, or 23 amino acid residues are deleted from the C-terminus to the N-terminal direction, starting from the amino acid at position 333 of SEQ ID NO: 13.

In addition, the present invention provides a polypeptide represented by the following Formula (II):

N-terminal extension domain-core domain-C-terminal extension domain    (II), in the above Formula (II), the core domain is a polypeptide comprising the amino acid sequence of SEQ ID NO: 37;

the N-terminal extension domain is a polypeptide comprising the amino acid sequence of SEQ ID NO: 39 in which 1 to 41 amino acids are consecutively deletable from the N-terminus to the C-terminal direction, starting from the amino acid at position 1 of SEQ ID NO: 39; and the C-terminal extension domain is a polypeptide comprising the amino acid sequence of SEQ ID NO: 41 in which 1 to 15 amino acids are consecutively deletable from the C-terminus to the N-terminal direction, starting from the amino acid at position 16 of SEQ ID NO: 41.

The core domain is a polypeptide comprising the amino acid sequence from position 154 to position 317 of the full-length Nkx3.2 protein. The full-length Nkx3.2 protein may include the amino acid sequence of SEQ ID NO: 7, and the core domain may include the amino acid sequence of SEQ ID NO: 37.

The N-terminal extension domain is a domain bound to the N-terminus of the above-mentioned core domain, and is a polypeptide comprising the amino acid sequence from position 112 to position 153 of the full-length Nkx3.2 protein. The N-terminal extension domain may include the amino acid sequence of SEQ ID NO: 39.

The N-terminal extension domain may be a polypeptide comprising the amino acid sequence of SEQ ID NO: 39, or a polypeptide comprising the amino acid sequence of SEQ ID NO: 39 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 amino acid residues are deleted from the N-terminus to the C-terminal direction, starting from the amino acid at position 1 of SEQ ID NO: 39. In embodiments of the present invention, the N-terminal extension domain may be a polypeptide comprising the amino acid sequence of SEQ ID NO: 39, or a polypeptide comprising the amino acid sequence of SEQ ID NO: 39 in which 11, 18, 38, or 41 amino acid residues are deleted from the N-terminus to the C-terminal direction, starting from the amino acid at position 1 of SEQ ID NO: 39.

The C-terminal extension domain is a domain bound to the C-terminus of the above-mentioned core domain, and is a polypeptide comprising the amino acid sequence from position 318 to position 333 of the full-length Nkx3.2 protein. The C-terminal extension domain may include the amino acid sequence of SEQ ID NO: 41.

The C-terminal extension domain may be a polypeptide comprising the amino acid sequence of SEQ ID NO: 41, or a polypeptide comprising the amino acid sequence of SEQ ID NO: 41 in which 1, 2, 3, 4, 5, 6, 7, 8, 9, 10, 11, 12, 13, 14, or 15 amino acid residues are deleted from the C-terminus to the N-terminal direction, starting from the amino acid at position 16 of SEQ ID NO: 41.

Specifically, the C-terminal extension domain may be a polypeptide comprising the amino acid sequence of SEQ ID NO: 41 in which 13 or 15 amino acid residues are deleted from the C-terminus to the N-terminal direction, starting from the amino acid at position 16 of SEQ ID NO: 41.

In embodiments of the present invention, the C-terminal extension domain may be a polypeptide comprising the amino acid sequence of SEQ ID NO: 41, or a polypeptide comprising the amino acid sequence of SEQ ID NO: 41 in which 3, 6, 9, 13, or 15 amino acid residues are deleted from the C-terminus to the N-terminal direction, starting from the amino acid at position 16 of SEQ ID NO: 41.

The polypeptides represented by the above Formula (I) or (II) are fragments of the Nkx3.2 protein and are not naturally present in living bodies. Nevertheless, the polypeptides are not easily degraded in vivo while having the activity comparable to the full-length Nkx3.2 protein, and thus can stay present in a body longer than the full-length Nkx3.2, exhibiting an excellent activity.

The present invention provides polynucleotides encoding the polypeptides represented by the above Formula (I) or (II).

The polynucleotides according to the present invention encodes the core domain, the N-terminal extension domain, and the C-terminal extension domain which may include, respectively, the nucleotide sequences of SEQ ID NO: 2 or 38, SEQ ID NO: 36 or 40, and SEQ ID NO: 6 or 42.

The polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 1, SEQ ID NO: 35, or SEQ ID NO: 5.

In addition, the polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 37, SEQ ID NO: 39, or SEQ ID NO: 41.

The present invention provides expression vectors comprising the polynucleotides.

The expression vector may be a plasmid vector, a cosmid vector, a bacteriophage vector, or a viral vector. The expression vector can be constructed by a person of ordinary skill in the art, such that the polynucleotides according to the present invention can be expressed and secreted therein.

In addition, the present invention provides host cells harboring the expression vectors.

The host cell is a cell transfected with an expression vector comprising the polynucleotide according to the present invention, and may be a prokaryotic cell or a eukaryotic cell. Specifically, the host cell may be a mammalian cell. The transfection can be carried out using the methods known in the art. Meanwhile, an example of the prokaryotic cell may be *E. coli*, and an example of the eukaryotic cell may be yeast. In addition, the mammalian cell may be NS/0 myeloma cells, 293 cells, Chinese hamster ovary cells (CHO cells), HeLa cells, CapT cells (human amniotic fluid-derived cells), or COS cells.

The present invention provides recombinant viruses comprising the polynucleotides provided herein.

The virus may be any one selected from the group consisting of an adenovirus, an adeno-associated virus (AAV), a retrovirus, a lentivirus, a herpes simplex virus, and a vaccinia virus. Specifically, the virus may be an adeno-associated virus (AAV). The adeno-associated virus is not limited to a specific serotype, and in some embodiments, the AAV may be any one of AAV1 to AAV9.

Since the adeno-associated virus (AAV) is capable of infecting non-dividing cells and has an ability to infect various types of cells, the adeno-associated virus is suitably used as a gene delivery system of the present invention. Details for preparation and uses of AAV vectors are described, for example, in U.S. Pat. Nos. 5,139,941 and 4,797,368.

Typically, the AAV can be produced by co-transfection of a plasmid comprising a gene sequence of interest which is flanked by two AAV terminal repeats and an expression plasmid comprising a wild-type AAV coding sequence that does not include the terminal repeats.

In embodiments of the present invention, the present inventors produced Nkx3.2 fragments, and found that the fragments are not degraded by Siah1 (FIG. 1). The inventors also found that NKx3.2 fragments provided herein induce the degradation of IκBα through binding to IκBα (FIGS. 2 and 3) and induce transcriptional activation of NF-κB (FIG. 4). In addition, the present inventors found that when the adeno-associated virus that includes the polynucleotide encoding the Nkx3.2 fragment is administered to degenerative arthritis-induced mice, damaged cartilage tissue is restored (FIGS. 7 and 8). Therefore, the Nkx3.2 fragments of the present invention can be effectively used for preventing or treating arthritis.

The present invention provides pharmaceutical compositions for preventing or treating arthritis, comprising a polypeptide provided herein as an active ingredient. Specifically, the present invention provides pharmaceutical compositions for preventing or treating arthritis, comprising a Nkx3.2 fragment provided herein as an active ingredient.

The Nkx3.2 fragment may be a polypeptide represented by the following Formula (I):

N-terminal extension domain-core domain-C-terminal extension domain    (I), in the above Formula (I), the core domain is a polypeptide comprising the amino acid sequence of SEQ ID NO: 1;

the N-terminal extension domain is a polypeptide comprising the amino acid sequence of SEQ ID NO: 35 in which 1 to 53 amino acids are consecutively deletable from the N-terminus to the C-terminal direction, starting from the amino acid at position 1 of SEQ ID NO: 35; and the C-terminal extension domain is a polypeptide comprising the amino acid sequence of SEQ ID NO: 5 in which 1 to 23 amino acids are consecutively deletable from the C-terminus to the N-terminal direction, starting from the amino acid at position 24 of SEQ ID NO: 5.

The core domain is a polypeptide comprising the amino acid sequence from position 166 to position 309 of the full-length Nkx3.2 protein. The full-length Nkx3.2 protein may include the amino acid sequence of SEQ ID NO: 7, and the core domain may include the amino acid sequence of SEQ ID NO: 1.

The N-terminal extension domain is a domain bound to the N-terminus of the above-mentioned core domain, and is a polypeptide comprising the amino acid sequence from position 112 to position 165 of the full-length Nkx3.2 protein. The N-terminal extension domain may include the amino acid sequence of SEQ ID NO: 35.

The N-terminal extension domain may be a polypeptide comprising the amino acid sequence of SEQ ID NO: 35, or a polypeptide comprising the amino acid sequence of SEQ ID NO: 35 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acid residues are deleted from the N-terminus to the C-terminal direction, starting from the amino acid at position 1 of SEQ ID NO: 35. In embodiments of the present invention, the N-terminal extension domain may be a polypeptide comprising the amino acid sequence of SEQ ID NO: 35, or a polypeptide comprising the amino acid sequence of SEQ ID NO: 35 in which 11, 18, 38, 41, 44, 47, 50, or 53 amino acid residues are deleted from the N-terminus to the C-terminal direction, starting from the amino acid at position 1 of SEQ ID NO: 35.

The C-terminal extension domain is a domain bound to a C-terminus of the above-mentioned core domain, and is a polypeptide comprising the amino acid sequence from position 310 to position 333 of the full-length Nkx3.2 protein. The C-terminal extension domain may include the amino acid sequence of SEQ ID NO: 5.

The C-terminal extension domain may be a polypeptide comprising the amino acid sequence of SEQ ID NO: 5, or a polypeptide comprising the amino acid sequence of SEQ ID NO: 5 in which 1, 2, 3, 4, 5, 6, 7, 8, 9, 10, 11, 12, 13, 14, 15, 16, 17, 18, 19, 20, 21, 22, or 23 amino acid residues are deleted from the C-terminus to the N-terminal direction, starting from the amino acid at position 24 of SEQ ID NO: 5.

Specifically, the C-terminal extension domain may be a polypeptide comprising the amino acid sequence of SEQ ID NO: 5, or a polypeptide comprising the amino acid sequence of SEQ ID NO: 5 in which 13, 14, 15, 16, 17, 18, 19, 20, 21, 22, or 23 amino acid residues are deleted from the C-terminus to the N-terminal direction, starting from the amino acid at position 24 of SEQ ID NO: 5.

In certain embodiments, the C-terminal extension domain may be a polypeptide comprising the amino acid sequence of SEQ ID NO: 5, or a polypeptide comprising the amino acid sequence of SEQ ID NO: 5 in which 13, 15, 17, 19, 21, or 23 amino acid residues are deleted from the C-terminus to the N-terminal direction, starting from the amino acid at position 24 of SEQ ID NO: 5.

Deletion of the amino acid residues may occur in either or both of the N-terminal extension domain and the C-terminal extension domain. In some embodiments, the polypeptide may include the amino acid sequence of SEQ ID NO: 13, 14, 20, 21, 22, 23, 24, 25, 26, 27, or 28.

The present invention provides a polypeptide comprising the amino acid sequence of SEQ ID NO: 13 or a fragment thereof. The fragment may be a polypeptide comprising the amino acid sequence of SEQ ID NO: 13 in which 1 to 53 amino acids are consecutively deleted from the N-terminus to the C-terminal direction, starting from the amino acid at position 1 of SEQ ID NO: 13. In addition, the fragment may be a polypeptide comprising the amino acid sequence of SEQ ID NO: 13 in which 1 to 23 amino acids are consecutively deleted from the C-terminus to the N-terminal direction, starting from the amino acid at position 333 of SEQ ID NO: 13.

In embodiments of the present invention, the polypeptide may include the amino acid sequence of SEQ ID NO: 13. In addition, the polypeptide may be a polypeptide comprising the amino acid sequence of SEQ ID NO: 13 in which 11, 18, 38, 41, 44, 47, 50, or 53 amino acid residues are deleted from the N-terminus to the C-terminal direction, starting from the amino acid at position 1 of SEQ ID NO: 13. In addition, the polypeptide may be a polypeptide comprising the amino acid sequence of SEQ ID NO: 13 in which 13, 15, 17, 19, 21, or 23 amino acid residues are deleted from the C-terminus to the N-terminal direction, starting from the amino acid at position 333 of SEQ ID NO: 13.

In addition, the Nkx3.2 fragment may be a polypeptide represented by the following Formula (II):

N-terminal extension domain-core domain-C-terminal extension domain    (II), in the above Formula (II), the core domain is a polypeptide comprising the amino acid sequence of SEQ ID NO: 37;

the N-terminal extension domain is a polypeptide comprising the amino acid sequence of SEQ ID NO: 39 in which 1 to 41 amino acids are consecutively deletable from the N-terminus to the C-terminal direction, starting from the amino acid at position 1 of SEQ ID NO: 39; and the C-terminal extension domain is a polypeptide comprising the amino acid sequence of SEQ ID NO: 41 in which 1 to 15 amino acids are consecutively deletable from the C-terminus to the N-terminal direction, starting from the amino acid at position 16 of SEQ ID NO: 41.

The core domain is a polypeptide comprising the amino acid sequence from position 154 to position 317 of the full-length Nkx3.2 protein. The full-length Nkx3.2 protein may include the amino acid sequence of SEQ ID NO: 7, and the core domain may include the amino acid sequence of SEQ ID NO: 37.

The N-terminal extension domain is a domain bound to the N-terminus of the above-mentioned core domain, and is a polypeptide comprising the amino acid sequence from position 112 to position 153 of the full-length Nkx3.2 protein. The N-terminal extension domain may include the amino acid sequence of SEQ ID NO: 39.

The N-terminal extension domain may be a polypeptide comprising the amino acid sequence of SEQ ID NO: 39, or a polypeptide comprising the amino acid sequence of SEQ ID NO: 39 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 amino acid residues are deleted from the N-terminus to the C-terminal direction, starting from the amino acid at position 1 of SEQ ID NO: 39. In embodiments of the present invention, the N-terminal extension domain may be a polypeptide comprising the amino acid sequence of SEQ ID NO: 39, or a polypeptide comprising the amino acid sequence of SEQ ID NO: 39 in which 11, 18, 38, or 41 amino acid residues are deleted from the N-terminus to the C-terminal direction, starting from the amino acid at position 1 of SEQ ID NO: 39.

The C-terminal extension domain is a domain bound to the C-terminus of the above-mentioned core domain, and is a polypeptide comprising the amino acid sequence from position 318 to position 333 of the full-length Nkx3.2 protein. The C-terminal extension domain may include the amino acid sequence of SEQ ID NO: 41.

The C-terminal extension domain may be a polypeptide comprising the amino acid sequence of SEQ ID NO: 41, or a polypeptide comprising the amino acid sequence of SEQ ID NO: 41 in which 1, 2, 3, 4, 5, 6, 7, 8, 9, 10, 11, 12, 13, 14, or 15 amino acid residues are deleted from the C-terminus to the N-terminal direction, starting from the amino acid at position 16 of SEQ ID NO: 41.

Specifically, the C-terminal extension domain may be a polypeptide comprising the amino acid sequence of SEQ ID NO: 41 in which 13 or 15 amino acid residues are deleted from the C-terminus to the N-terminal direction, starting from the amino acid at position 16 of SEQ ID NO: 41.

In embodiments of the present invention, the C-terminal extension domain may be a polypeptide comprising the amino acid sequence of SEQ ID NO: 41, or a polypeptide comprising the amino acid sequence of SEQ ID NO: 41 in which 3, 6, 9, 13, or 15 amino acid residues are deleted from the C-terminus to the N-terminal direction, starting from the amino acid at position 16 of SEQ ID NO: 41.

The polypeptides represented by the above Formula (I) or (II) are fragments of the Nkx3.2 protein and are not naturally present in living bodies. However, the polypeptide is not easily degraded in vivo while having activity comparable to the full-length Nkx3.2 protein, and thus can stay present in a body longer than the full-length Nkx3.2, exhibiting an excellent activity.

The Nkx3.2 fragment can be obtained by a host cell transfected with an expression vector that includes a polynucleotide encoding the polypeptide represented by (I) or (II).

The polynucleotide encodes the above-mentioned core domain, N-terminal extension domain, and C-terminal extension domain which may include the nucleotide sequences of SEQ ID NO: 2 or 38, SEQ ID NO: 36 or 40, and SEQ ID NO: 6 or 42, respectively.

The polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 1, SEQ ID NO: 35, or SEQ ID NO: 5.

In addition, the polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 37, SEQ ID NO: 39, or SEQ ID NO: 41.

The expression vector may be a plasmid vector, a cosmid vector, a bacteriophage vector, or a viral vector. The expression vector can be constructed by a person of ordinary skill in the art, such that the polynucleotide according to the present invention can be expressed and secreted therein.

The host cell is a cell transfected with an expression vector comprising the polynucleotide according to the present invention, and may be a prokaryotic cell or a eukaryotic cell. Specifically, the host cell may be a mammalian cell. The transfection can be carried out by methods known in the art. Meanwhile, an example of the prokaryotic cell may be *E. coli*, and an example of the eukaryotic cell may be yeast. In addition, the mammalian cell may be NS/0 myeloma cells, 293 cells, Chinese hamster ovary cells (CHO cells), HeLa cells, CapT cells (human amniotic fluid-derived cells), or COS cells.

The arthritis may be any one selected from the group consisting of osteoarthritis, rheumatoid arthritis, degenerative arthritis, gouty arthritis, juvenile arthritis, senescent arthritis, reactive arthritis, and combinations thereof.

The pharmaceutical composition may include 0.1% to 99% by weight, 1% to 90% by weight, and 10% to 80% by weight of the polypeptide according to the present invention as an active ingredient, relative to the total weight of the pharmaceutical composition. In addition, the pharmaceutical composition of the present invention may further include one or more active ingredients which exhibit the same or similar function in addition to the above-described active ingredient.

The pharmaceutical composition according to the present invention may further include one or more pharmaceutically acceptable carriers for administration in addition to the above-described active ingredients.

The dosage of the pharmaceutical composition for preventing or treating arthritis which includes the Nkx 3.2 fragments as an active ingredient may be adjusted depending on various factors comprising the type of the disease, severity of the disease, types and contents of active ingredients and other ingredients included in the pharmaceutical composition, the type of formulation, patient's age, body weight, general health condition, sex, and diet, times of administration, routes of administration, duration of treatment, and drugs simultaneously used.

However, for a desired effect, the dosage of the polypeptide included in the pharmaceutical composition according to the present invention may be 0.0001 to 100 mg/kg. Here, administration may be carried out once a day or divided into several times.

The present invention provides a pharmaceutical composition for preventing or treating arthritis, comprising the recombinant virus as an active ingredient. Specifically, the present invention provides a pharmaceutical composition for preventing or treating arthritis, comprising, as an active ingredient, a recombinant virus that includes a polynucleotide encoding the Nkx3.2 fragment.

The polynucleotide loaded on the recombinant virus may encode a polypeptide represented by the following Formula (I):

N-terminal extension domain-core domain-C-terminal extension domain    (I), in the above Formula (I), the core domain is a polypeptide comprising the amino acid sequence of SEQ ID NO: 1;

the N-terminal extension domain is a polypeptide comprising the amino acid sequence of SEQ ID NO: 35 in which 1 to 53 amino acids are consecutively deletable from the N-terminus to the C-terminal direction, starting from the amino acid at position 1 of SEQ ID NO: 35; and the C-terminal extension domain is a polypeptide comprising the amino acid sequence of SEQ ID NO: 5 in which 1 to 23 amino acids are consecutively deletable from the C-terminus to the N-terminal direction, starting from the amino acid at position 24 of SEQ ID NO: 5.

The core domain is a polypeptide comprising the amino acid sequence from position 166 to position 309 of the full-length Nkx3.2 protein. The full-length Nkx3.2 protein may include the amino acid sequence of SEQ ID NO: 7, and the core domain may include the amino acid sequence of SEQ ID NO: 1.

The N-terminal extension domain is a domain bound to the N-terminus of the above-mentioned core domain, and is a polypeptide comprising the amino acid sequence from position 112 to position 165 of the full-length Nkx3.2 protein. The N-terminal extension domain may include the amino acid sequence of SEQ ID NO: 35.

The N-terminal extension domain may be a polypeptide comprising the amino acid sequence of SEQ ID NO: 35, or a polypeptide comprising the amino acid sequence of SEQ ID NO: 35 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acid residues are deleted from the N-terminus to the C-terminal direction, starting from the amino acid at position 1 of SEQ ID NO: 35.

In embodiments of the present invention, the N-terminal extension domain may be a polypeptide comprising the amino acid sequence of SEQ ID NO: 35, or a polypeptide comprising the amino acid sequence of SEQ ID NO: 35 in which 11, 18, 38, 41, 44, 47, 50, or 53 amino acid residues are deleted from the N-terminus to the C-terminal direction, starting from the amino acid at position 1 of SEQ ID NO: 35.

The C-terminal extension domain is a domain bound to the C-terminus of the above-mentioned core domain, and is a polypeptide comprising the amino acid sequence from position 310 to position 333 of the full-length Nkx3.2 protein. The C-terminal extension domain may include the amino acid sequence of SEQ ID NO: 5.

The C-terminal extension domain may be a polypeptide comprising the amino acid sequence of SEQ ID NO: 5, or a polypeptide comprising the amino acid sequence of SEQ ID NO: 5 in which 1, 2, 3, 4, 5, 6, 7, 8, 9, 10, 11, 12, 13, 14, 15, 16, 17, 18, 19, 20, 21, 22, or 23 amino acid residues are deleted from the C-terminus to the N-terminal direction, starting from the amino acid at position 24 of SEQ ID NO: 5.

Specifically, the C-terminal extension domain may be a polypeptide comprising the amino acid sequence of SEQ ID NO: 5, or a polypeptide comprising the amino acid sequence of SEQ ID NO: 5 in which 13, 14, 15, 16, 17, 18, 19, 20, 21, 22, or 23 amino acid residues are deleted from the C-terminus to the N-terminal direction, starting from the amino acid at position 24 of SEQ ID NO: 5.

In embodiments of the present invention, the C-terminal extension domain may be a polypeptide comprising the amino acid sequence of SEQ ID NO: 5, or a polypeptide comprising the amino acid sequence of SEQ ID NO: 5 in which 13, 15, 17, 19, 21, or 23 amino acid residues are deleted from the C-terminus to the N-terminal direction, starting from the amino acid at position 24 of SEQ ID NO: 5.

Deletion of the amino acid residues may occur in either or both of the N-terminal extension domain and the C-terminal extension domain. In embodiments of the present invention, the polypeptide may include the amino acid sequence of SEQ ID NO: 13, 14, 20, 21, 22, 23, 24, 25, 26, 27, or 28.

In addition, the polynucleotide loaded on the recombinant virus may encode a polypeptide represented by the following Formula (II):

N-terminal extension domain-core domain-C-terminal extension domain    (II),

In the above Formula (II), the core domain is a polypeptide comprising the amino acid sequence of SEQ ID NO: 37;

the N-terminal extension domain is a polypeptide comprising the amino acid sequence of SEQ ID NO: 39 in which 1 to 41 amino acids are consecutively deletable from the N-terminus to the C-terminal direction, starting from the amino acid at position 1 of SEQ ID NO: 39; and the C-terminal extension domain is a polypeptide comprising the amino acid sequence of SEQ ID NO: 41 in which 1 to 15 amino acids are consecutively deletable from the C-terminus to the N-terminal direction, starting from the amino acid at position 16 of SEQ ID NO: 41.

The core domain refers to a polypeptide comprising the amino acid sequence from position 154 to position 317 of the full-length Nkx3.2 protein. The full-length Nkx3.2 protein may include the amino acid sequence of SEQ ID NO: 7, and the core domain may include the amino acid sequence of SEQ ID NO: 37.

The N-terminal extension domain is a domain bound to the N-terminus of the above-mentioned core domain, and is a polypeptide comprising the amino acid sequence from position 112 to position 153 of the full-length Nkx3.2 protein. The N-terminal extension domain may include the amino acid sequence of SEQ ID NO: 39.

The N-terminal extension domain may be a polypeptide comprising the amino acid sequence of SEQ ID NO: 39, or a polypeptide comprising the amino acid sequence of SEQ ID NO: 39 in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 amino acid residues are deleted from the N-terminus to the C-terminal direction, starting from the amino acid at position 1 of SEQ ID NO: 39. In embodiments of the present invention, the N-terminal extension domain may be a polypeptide comprising the amino acid sequence of SEQ ID NO: 39, or a polypeptide comprising the amino acid sequence of SEQ ID NO: 39 in which 11, 18, 38, or 41 amino acid residues are deleted from the N-terminus to the C-terminal direction, starting from the amino acid at position 1 of SEQ ID NO: 39.

The C-terminal extension domain is a domain bound to the C-terminus of the above-mentioned core domain, and is a polypeptide comprising the amino acid sequence from position 318 to position 333 of the full-length Nkx3.2 protein. The C-terminal extension domain may include the amino acid sequence of SEQ ID NO: 41.

The C-terminal extension domain may be a polypeptide comprising the amino acid sequence of SEQ ID NO: 41, or a polypeptide comprising the amino acid sequence of SEQ ID NO: 41 in which 1, 2, 3, 4, 5, 6, 7, 8, 9, 10, 11, 12, 13, 14, or 15 amino acid residues are deleted from the C-terminus to the N-terminal direction, starting from the amino acid at position 16 of SEQ ID NO: 41.

Specifically, the C-terminal extension domain may be a polypeptide comprising the amino acid sequence of SEQ ID NO: 41 in which 13 or 15 amino acid residues are deleted from the C-terminus to the N-terminal direction, starting from the amino acid at position 16 of SEQ ID NO: 41.

In an embodiment of the present invention, the C-terminal extension domain may be a polypeptide comprising the amino acid sequence of SEQ ID NO: 41, or a polypeptide comprising the amino acid sequence of SEQ ID NO: 41 in which 3, 6, 9, 13, or 15 amino acid residues are deleted from the C-terminus to the N-terminal direction, starting from the amino acid at position 16 of SEQ ID NO: 41.

The polypeptide represented by the above Formula (I) or (II) is a fragment of the Nkx3.2 protein and is not present in vivo. However, the polypeptide is not easily degraded in vivo while having the same activity as the full-length Nkx3.2 protein, and thus is present in a body longer than the full-length Nkx3.2 to exhibit excellent activity.

A recombinant virus that includes a polynucleotide encoding the Nkx3.2 fragment can be obtained through a host cell transfected with an expression vector that includes a polynucleotide encoding the polypeptide represented by (I) or (II).

The polynucleotide encodes the above-mentioned core domain, N-terminal extension domain, and C-terminal extension domain which may include the nucleotide sequences of SEQ ID NO: 2 or 38, SEQ ID NO: 36 or 40, and SEQ ID NO: 6 or 42, respectively.

The polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 1, SEQ ID NO: 35, or SEQ ID NO: 5.

In addition, the polynucleotide may include a polynucleotide that encodes a fragment obtained by deletion of amino acid residues in the N-terminal extension domain and C-terminal extension domain as described above. Here, the polynucleotide may include a polynucleotide substituted with another nucleotide sequence that expresses the polypeptide of SEQ ID NO: 37, SEQ ID NO: 39, or SEQ ID NO: 41.

The polynucleotide may include a nucleotide sequence encoding the amino acid sequence of SEQ ID NO: 13, 14, 20, 21, 22, 23, 24, 25, 26, 27, or 28.

The virus may be any one selected from the group consisting of an adenovirus, an adeno-associated virus (AAV), a retrovirus, a lentivirus, a herpes simplex virus, and a vaccinia virus. Specifically, the virus may be an adeno-associated virus (AAV). The adeno-associated virus is not limited to a specific serotype, and preferably, may be any one of AAV1 to AAV9.

Since the adeno-associated virus (AAV) is capable of infecting non-dividing cells and has an ability to infect various types of cells, the adeno-associated virus is suitably used as a gene delivery system of the present invention. Details for preparation and uses of AAV vectors are described in U.S. Pat. Nos. 5,139,941 and 4,797,368.

Typically, the AAV can be produced by co-transfection of a plasmid comprising a gene sequence of interest which is flanked by two AAV terminal repeats and an expression plasmid comprising a wild-type AAV coding sequence which does not have the terminal repeats.

The arthritis may be any one selected from the group consisting of osteoarthritis, rheumatoid arthritis, degenerative arthritis, gouty arthritis, juvenile arthritis, senescent arthritis, reactive arthritis, and combinations thereof.

The pharmaceutical composition according to the present invention may further include one or more pharmaceutically acceptable carriers for administration in addition to the above-described active ingredients.

The dosage of the pharmaceutical composition for preventing or treating arthritis which includes, as an active ingredient, a recombinant virus that includes a polynucleotide encoding the Nkx 3.2 fragment may be adjusted depending on various factors including the type of the disease, severity of the disease, types and contents of active ingredients and other ingredients included in the pharmaceutical composition, the type of formulation, patient's age, body weight, general health condition, sex, and diet, times of administration, routes of administration, duration of treatment, and drugs simultaneously used.

However, for a desired effect, the recombinant virus included in the pharmaceutical composition according to the present invention may be administered in an amount of $1.0 \times 10^5$ to $1.0 \times 10^{15}$ viral genome per day in the case of adults. Specifically, the dosage of the pharmaceutical composition of the present invention may be such that administration is carried out in an amount of $1.0 \times 10^5$ to $1.0 \times 10^{15}$, $1.0 \times 10^7$ to $1.0 \times 10^{13}$, $1.0 \times 10^8$ to $1.0 \times 10^{12}$, or $1.0 \times 10^9$ to $1.0 \times 10^{10}$ per day in the case of adults.

The present invention provides a method of preventing or treating arthritis, comprising the step of administering the pharmaceutical composition to a subject in need thereof. Specifically, the present invention provides a method of preventing or treating arthritis, comprising the step of administering, to a subject in need thereof, a pharmaceutical composition for preventing or treating arthritis, which includes, as an active ingredient, the Nkx3.2 fragment or a recombinant virus that includes a polynucleotide encoding the Nkx 3.2 fragment.

The subject may be a mammal, in particular, a human. The route of administration can be appropriately selected by a person skilled in the art in consideration of an administration method, volume and viscosity of body fluid, and the like. Specifically, the pharmaceutical composition may be intra-articularly administered.

The pharmaceutical composition may be intra-articularly administered. As used herein, the term "intra-articularly" means that administration is carried out via a lumen enclosed by an articular capsule, which is a gap between bones in a joint. There are various methods to carry out intra-articular administration. For example, there is a method in which a patient is asked to bend one knee 90 degrees in a state of lying down at a posture looking at the ceiling, and a syringe is intra-articularly inserted. In this posture, the inside and the outside joint boundaries can be relatively easily distinguished by hand. Injection can be carried out at either or both of the inside and the outside joint boundaries, and is mostly carried out toward the inside joint boundary. In addition, there is also a method of carrying out injection at a posture where a knee is stretched. For both postures, when the syringe is correctly inserted into a predetermined injection site, the injection solution may be injected with little resistance. However, when, at the time of pressing a syringe, drugs do not enter well, and a sense of resistance is recognized or a patient complains of severe pain, the injection site of the syringe should be adjusted.

The present invention provides a method of producing an Nkx3.2 fragment with increased stability in a body, comprising the step of deleting any one region of a polypeptide comprising the amino acid sequence of SEQ ID NO: 7, which is selected from the group consisting of an N-terminal region and a C-terminal region, and a combination thereof.

Deletion of the N-terminal region may be such that 1 to 165 amino acids are consecutively deleted from the N-terminus to the C-terminal direction, starting from the amino acid at position 1 of SEQ ID NO: 7. Specifically, the deletion may be such that 1 to 53 amino acids are consecutively deleted from the N-terminus to the C-terminal direction, starting from the amino acid at position 112 of SEQ ID NO: 7. In an embodiment of the present invention, the deletion of the N-terminal region may be such that 11, 18, 38, 41, 44, 47, 50, or 53 amino acid residues are deleted from the N-terminus to the C-terminal direction, starting from the amino acid at position 112 of SEQ ID NO: 7.

Deletion of the C-terminal region may be such that 1 to 23 amino acids are consecutively deleted from the C-terminus to the N-terminal direction, starting from the amino acid at position 333 of SEQ ID NO: 7. In an embodiment of the present invention, the deletion of the C-terminal region may be such that 13, 15, 17, 19, 21, or 23 amino acid residues are deleted from the C-terminus to the N-terminal direction, starting from the amino acid at position 333 of SEQ ID NO: 7.

The deletion of the amino acid residue may occur at either or both of the N-terminal region and the C-terminal region. In an embodiment of the present invention, the Nkx3.2 fragment may include the amino acid sequence of SEQ ID NO: 13, 14, 20, 21, 22, 23, 24, 25, 26, 27, or 28.

The deletion of the amino acid residues can be carried out with an appropriate method by a person skilled in the art. The Nkx3.2 fragments with increased stability in a body produced by the above method are not easily degraded in vivo by Siah1, and thus may be present in a body longer than the wild type Nkx3.2 protein.

MODES FOR CARRYING OUT THE INVENTION

Hereinafter, the present invention will be described in detail by the following examples. However, the following examples are intended merely to illustrate the present invention, and the present invention is not limited thereto.

Example 1. Construction of Vectors Expressing Nkx3.2 Fragments

In order to obtain variants which are resistant to proteolysis mediated by Siah1, vectors expressing Nkx3.2 fragments were constructed by the following method.

Specifically, the Nkx3.2 gene having the nucleotide sequence represented by SEQ ID NO: 8 was used as a template and amplified using a Lamp Pfu DNA polymerase (Cat. #LP116-250, BIOFACT Co., Ltd., Korea) according to the manufacturer's protocol. Each of the amplified PCR products was cleaved with restriction enzymes EcoRI (Cat. #FD0274, Thermo Fisher Scientific Inc., USA), and XhoI (Cat. #FD0694, Thermo Fisher Scientific Inc., USA) or XbaI (Cat. #FD0684, Thermo Fisher Scientific Inc., USA), and respectively, inserted into a pCS expression vector (Addgene Cat #17095) using a T4 ligase (Cat. #EL0011, Thermo Fisher Scientific Inc., USA).

Consequently, expression vectors expressing 20 kinds of Nkx3.2 fragments were constructed as shown in Table 1 below.

TABLE 1

| Name | Feature | SEQ ID NO |
| --- | --- | --- |
| Nkx3.2 (1-333) | Full-length Nkx3.2 | SEQ ID NO: 7 |
| Nkx3.2 (1-320) | Nkx3.2 fragment containing 1st to 320th amino acids | SEQ ID NO: 9 |
| Nkx3.2 (1-307) | Nkx3.2 fragment containing 1st to 307th amino acids | SEQ ID NO: 10 |
| Nkx3.2 (42-333) | Nkx3.2 fragment containing 42nd to 333rd amino acids | SEQ ID NO: 11 |
| Nkx3.2 (99-333) | Nkx3.2 fragment containing 99th to 333rd amino acids | SEQ ID NO: 12 |
| Nkx3.2 (112-333) | Nkx3.2 fragment containing 112th to 333rd amino acids | SEQ ID NO: 13 |
| Nkx3.2 (123-333) | Nkx3.2 fragment containing 123rd 333rd amino acids | SEQ ID NO: 14 |
| Nkx3.2 (99-330) | Nkx3.2 fragment containing 99th to 330th amino acids | SEQ ID NO: 15 |
| Nkx3.2 (99-327) | Nkx3.2 fragment containing 99th to 327th amino acids | SEQ ID NO: 16 |
| Nkx3.2 (99-320) | Nkx3.2 fragment containing 99th to 320th amino acids | SEQ ID NO: 17 |
| Nkx3.2 (105-327) | Nkx3.2 fragment containing 105th to 327th amino acids | SEQ ID NO: 18 |
| Nkx3.2 (110-324) | Nkx3.2 fragment containing 110th to 324th amino acids | SEQ ID NO: 19 |
| Nkx3.2 (112-320) | Nkx3.2 fragment containing 112th to 320th amino acids | SEQ ID NO: 20 |
| Nkx3.2 (123-320) | Nkx3.2 fragment containing 123rd 320th amino acids | SEQ ID NO: 21 |
| Nkx3.2 (130-320) | Nkx3.2 fragment containing 130th to 320th amino acids | SEQ ID NO: 22 |
| Nkx3.2 (150-320) | Nkx3.2 fragment containing 150th to 320th amino acids | SEQ ID NO: 23 |
| Nkx3.2 (153-318) | Nkx3.2 fragment containing 153rd 318th amino acids | SEQ ID NO: 24 |

TABLE 1-continued

| Name | Feature | SEQ ID NO |
|---|---|---|
| Nkx3.2 (156-316) | Nkx3.2 fragment containing 156th to 316th amino acids | SEQ ID NO: 25 |
| Nkx3.2 (159-314) | Nkx3.2 fragment containing 159th to 314th amino acids | SEQ ID NO: 26 |
| Nkx3.2 (162-312) | Nkx3.2 fragment containing 162nd to 312th amino acids | SEQ ID NO: 27 |
| Nkx3.2 (165-310) | Nkx3.2 fragment containing 165th to 310th amino acids | SEQ ID NO: 28 |

Example 2. Selection of Nkx3.2 Fragments Resistant to Proteolysis Mediated by Siah1

Using the expression vectors expressing the Nkx3.2 fragments as constructed in Example 1, Nkx3.2 fragments which are not degraded by Siah1 were selected by the following method.

First, Siah1 (SEQ ID NO: 29; GenBank Accession No. AAH35562.1) was amplified by PCR in the same condition and method as described in Example 1, and the amplified PCR product was cleaved with EcoRI and NcoI. The resulting product was inserted into a pCS 3HA expression vector (Addgene plasmid #17095, a vector with a 3-HA epitope tag inserted between EcoRI and ClaI sites of pCS2P+), which had been cleaved with the same restriction enzymes and includes a tag in which the human influenza hemagglutinin (HA) amino acid sequence (SEQ ID NO: 33; YPYDVPDYA) is repeated three times, to construct an expression vector expressing Siah1.

Meanwhile, 293T kidney cell line (Cat. #CRL-3216, ATCC, USA) was cultured in a DMEM (Dulbecco's modified Eagle's medium) medium supplemented with 10% (v/v) fetal bovine serum (FBS) at a condition of 37° C. and 5% $CO_2$. The prepared cells were dispensed on a 60×15 mm cell culture plate so that the number of cells was $5×10^5$. The cells were transiently transfected using 2 μg of the expression vector expressing Nkx3.2, and 4 μg of each of the expression vectors expressing the Nkx3.2 fragments, respectively, together with 2 μg of the expression vector expressing Siah1. The transfection was carried out using VivaMagic (Cat. #VM001, VIVAGEN CO., LTD., Korea) according to the manufacturer's protocol.

The entire protein was isolated from the transfected cells and quantitated using a Bio-Rad Laboratories protein kit (Cat. #500-0116, Bio-Rad Laboratories, Inc., USA). Then, western blotting for each of Nkx3.2, Siah1, and β-actin was carried out by a conventional method. Here, an anti-Nkx3.2 antibody (Cat. #Ab83288, Abcam, Great Britain), an anti-HA antibody (Cat. #11583816001, Roche, Switzerland), an anti-Myc antibody (Cat. #11667149001, Roche, Switzerland), and an anti-β-actin antibody (Cat. #LF-PA0207, AbFrontier, Korea) were diluted at 1:1,000, 1:5,000, 1:5,000, and 1:5,000, respectively, in a TBST buffer containing 3% (v/v) bovine serum albumin (BSA), and used. As a result, photographs of western blotting bands are illustrated in FIG. 1, which is summarized in Table 2 below.

TABLE 2

| Name | SEQ ID NO | Degradation by Siah1 | |
|---|---|---|---|
| Nkx3.2(1-333) | SEQ ID NO: 7 | +++ | ○ |
| Nkx3.2(1-320) | SEQ ID NO: 9 | + | x |
| Nkx3.2(1-307) | SEQ ID NO: 10 | − | x |
| Nkx3.2(42-333) | SEQ ID NO: 11 | +++ | ○ |
| Nkx3.2(99-333) | SEQ ID NO: 12 | ++ | x |
| Nkx3.2(112-333) | SEQ ID NO: 13 | ++ | x |
| Nkx3.2(123-333) | SEQ ID NO: 14 | − | x |
| Nkx3.2(99-330) | SEQ ID NO: 15 | +++ | ○ |
| Nkx3.2(99-327) | SEQ ID NO: 16 | +++ | ○ |
| Nkx3.2(99-320) | SEQ ID NO: 17 | + | x |
| Nkx3.2(105-327) | SEQ ID NO: 18 | ++ | ○ |
| Nkx3.2(110-324) | SEQ ID NO: 19 | +++ | ○ |
| Nkx3.2(112-320) | SEQ ID NO: 20 | − | x |
| Nkx3.2(123-320) | SEQ ID NO: 21 | − | x |
| Nkx3.2(130-320) | SEQ ID NO: 22 | − | x |
| Nkx3.2(150-320) | SEQ ID NO: 23 | − | x |
| Nkx3.2(153-318) | SEQ ID NO: 24 | − | x |
| Nkx3.2(156-316) | SEQ ID NO: 25 | ++ | x |
| Nkx3.2(159-314) | SEQ ID NO: 26 | ++ | x |
| Nkx3.2(162-312) | SEQ ID NO: 27 | ++ | x |
| Nkx3.2(165-310) | SEQ ID NO: 28 | ++ | x |

As illustrated in FIG. 1 and shown in Table 2, unlike the full-length Nkx3.2 (1-333), a degradation of Nkx3.2 protein by Siah1 did not occur in the fragments Nkx3.2 (1-320), Nkx3.2 (1-307), Nkx 3.2 (123-333), Nkx 3.2 (99-320), Nkx 3.2 (112-320), Nkx 3.2 (123-320), Nkx 3.2 (130-320), Nkx3.2 (150-320), and Nkx3.2 (153-318).

Example 3. Identifying Whether Nkx3.2 Fragments Bind to IκBα

Nkx3.2 induces NF-κB activation through binding to IκBα. Thus, immunoprecipitation was used to identify whether the fragments Nkx 3.2 (112-320), Nkx 3.2 (123-320), Nkx 3.2 (130-320), Nkx 3.2 (150-320), and Nkx 3.2 (153-318) bind to IκBα.

First, IκBα (SEQ ID NO: 31; GenBank Accession No. CAB65556) was amplified by PCR in the same condition and method as described in Example 1, and the amplified PCR product was cleaved with EcoRI and XbaI. The resulting product was inserted into a pCS 6Myc expression vector (Addgene plasmid #17095, a vector with 6-Myc epitope tag inserted between EcoRI and ClaI sites of pCS2P+), which had been cleaved with the same restriction enzymes and includes a tag in which the Myc amino acid sequence (SEQ ID NO: 34: EQKLISEEDL) is repeated six times, to construct an expression vector expressing IκBα.

Then, 293T kidney cell line was transfected in the same condition and method as described in Example 2 using 8 μg of the expression vector expressing Nkx3.2 (1-333) and each of the expression vectors expressing the fragments, respectively, as produced in Example 1, together with an equal amount of the expression vector expressing IκBα. Here, in order to prevent the IκBα protein from being degraded by the Nkx3.2 protein, MG132 (Cat. #474790, Merck Millipore, Germany), which is a proteasome-degradation suppressor, was added at a concentration of 20 μM. After 6 hours, the entire protein was isolated from the cells, and immunoprecipitation was carried out by a conventional method using an anti-Myc antibody that recognizes the Myc with which IκBα is labeled. Then, western blotting was carried out using the antibodies as described above. Photographs of the obtained results are illustrated in FIG. 2.

As illustrated in FIG. 2, similar to the full-length Nkx3.2 (1-333), the bands were formed for the fragments Nkx 3.2 (112-320), Nkx 3.2 (123-320), Nkx 3.2 (130-320), Nkx 3.2 (150-320), and Nkx 3.2 (153-318). Therefore, the Nkx3.2 fragments were identified to have the function of binding to IκBα to form a complex, which is necessarily required for activation of NF-κB.

Example 4. Identifying Whether IκBα Protein is Degraded by Nkx3.2 Fragments

Nkx3.2 binds to IκBα, and thus promotes ubiquitination and degradation of IκBα by proteasome. Accordingly, western blotting was carried out to identify whether the fragments Nkx3.2 (112-320), Nkx3.2 (123-320), Nkx3.2 (130-320), Nkx3.2 (150-320), and Nkx3.2 (153-318) maintain such activity.

Meanwhile, ATDC5 cartilage cell line (Cat. #RCB0565, Riken, Japan) was cultured in a DMEM/F12 (Dulbecco's modified Eagle's medium: Nutrient Mixture F-12) medium supplemented with 10% (v/v) fetal bovine serum at a condition of 37° C. and 5% $CO_2$. The prepared cells were dispensed on a 90×20 mm cell culture plate so that the number of cells was $5\times10^5$. The cells were transiently transfected using 4 μg of the expression vector expressing Nkx3.2 (1-333) and 8 μg of each of the expression vectors expressing the Nkx3.2 fragments, respectively, together with 1 μg of the expression vector expressing IκBα. The transfection was carried out using VivaMagic (Cat. #VM001, VIVAGEN CO., LTD., Korea) according to the manufacturer's protocol.

A subsequent process was such that western blotting was carried out in the same condition and method as described in Example 2, and photographs of the obtained results are illustrated in FIG. 3.

As shown in FIG. 3, bands with an intensity similar to the full-length Nkx3.2 (1-333) were formed for the fragments Nkx 3.2 (112-320), Nkx 3.2 (123-320), Nkx 3.2 (130-320), Nkx 3.2 (150-320), and Nkx3.2 (153-318). Hence, the Nkx3.2 fragments are identified to induce proteolysis of IκBα at the same level as the full-length Nkx3.2.

Example 5. Identifying Whether Transcriptional Function of NF-κB is Activated by Nkx3.2 Fragments Nkx3.2 suppresses cell death of chondrocytes by inducing NF-κB activation. Thus, in order to measure the NF-κB activation by Nkx3.2 fragments, a polynucleotide sequence in which the NF-κB-specific DNA binding site (SEQ ID NO: 35: GGGAATTTCC) is repeated four times was inserted into a pGL3-Basic vector (Cat. #E1751, Promega, USA) using MluI and XhoI to construct a 4×-κB-Luc expression vector. Further, the expression vector was used to measure activation of transcriptional function of NF-κB by Nkx3.2 by analyzing the luciferase activity.

First, 293T kidney cell line was transiently transfected using, respectively, 200 ng of the expression vector expressing the full-length Nkx3.2 (1-333) and each of the expression vectors expressing the Nkx3.2 fragments, 100 ng of the 4×-κB-Luc expression vector, and 20 ng of a pRL-TK expression vector (Cat. #E2241, Promega, USA).

Transfection was carried out using VivaMagic according to the manufacturer's protocol. After 24 hours, the luciferase assay was carried out using the Dual-Luciferase Reporter Assay System (Cat. #E1910, Promega, USA) according to the manufacturer's protocol.

Specifically, a culture of the transfected 293T kidney cell line was removed and washed with 1×PBS. 150 μl of 1× passive lysis buffer (PLB) was added thereto, and the cells were lysed at room temperature for 15 minutes. To 10 μl of the cell lysate, 50 μl of LAR II was added and the resultant was allowed to react. Then, the firefly luciferase activity was measured. To this, 50 μl of Stop & Glo was added and *Renilla* luciferase activity was measured. In the experimental results, for each sample, the *Renilla* luciferase activity was normalized to the firefly luciferase activity, and an average of percentages therefor is illustrated in FIG. 4.

As shown in FIG. 4, when the luciferase activity in the cells transfected with only the pCS2 vector as a negative control is set as 1, not only the full-length Nkx3.2 (1-333) but also the fragments Nkx3.2 (112-320), NKx3.2 (123-320), Nkx3.2 (130-320), Nkx3.2 (150-320), and Nkx3.2 (153-318) exhibited significantly increased luciferase activity. Thus, the Nkx3.2 fragments are identified to possess the function of activating the transcriptional function of NF-κB at the level similar to the full-length Nkx3.2.

Example 6: Identification of the Improved Therapeutic Efficacy of Nkx3.2 Fragments Against Degenerative Arthritis Through the above-described in vitro experiments, functional superiority of the Nkx3.2 fragments as compared with the full-length Nkx3.2 was identified. Accordingly, in order to identify the improved in vivo function of the Nkx3.2 fragments, the therapeutic efficacy of the Nkx3.2 fragment (123-320) and the full-length Nkx3.2 (1-333) against degenerative arthritis was compared and analyzed. For this purpose, a mouse model in which degenerative arthritis was induced through a surgical procedure called destabilization of medial meniscus (DMM) was selected. A process for carrying out the experiment is schematically illustrated in FIG. 6.

Specifically, the medial meniscus ligament in the knee tissue was cut to induce structural destabilization of the medial meniscus, and thus the femoral cartilage and the tibia cartilage were caused to collide against each other, so that cartilage damage was induced, thereby inducing degenerative arthritis. For a control, an animal group for which the outer skin and the inner skin of the knee were dissected and sutured by a mock surgery was used. The animal group for which degenerative arthritis were induced and the control for which the mock surgery were performed were grown for 8 weeks. Then, an adeno-associated virus (AAV) expressing the Nkx3.2 fragment (123-320) or the full-length Nkx3.2 (1-333), or an empty vector AAV was intra-articularly injected into the corresponding knee, and the animal groups were grown for 4 weeks. A progression degree of degenerative arthritis was analyzed by histopathological analysis.

For the histopathological analysis, a safranin-O staining method was employed. Safranin-O is a cationic compound stain and effectively adheres to an anionic group of cartilage heparan sulfate proteoglycan so that red color is exhibited. A reddish dark-stained area is evaluated to be cartilage tissue in a healthy condition. Conversely, a part that exhibits weak or no safranin-O staining, and a part with damaged tissue are interpreted as lesions in which the pathology of degenerative arthritis has progressed.

As shown in FIG. 7, in the case of the control group in which the empty vector AAV is intra-articularly injected, an extremely severe cartilage damage and degeneration phenomenon were observed regardless of the amount of viral particles administered.

In the case of the comparison group in which AAV expressing the full-length Nkx3.2 (1-333) is intra-articularly injected, significant therapeutic efficacy against degenerative arthritis was observed only in the AAV-administered group at $1\times10^{10}$.

On the contrary, in the case of the experimental group in which AAV expressing the NKx3.2 fragment (123-320) is intra-articularly injected, a superior therapeutic effect against degenerative arthritis was exhibited from the AAV-administered group at $1.25\times10^9$, which is the lowest dose. That is, in the case of the Nkx3.2 fragment (123-320), the therapeutic efficacy against degenerative arthritis is identified to be improved by at least 10 times, compared with the full-length Nkx3.2 (1-333).

All data obtained through the histopathological analysis were quantitatively evaluated, and the results are graphically illustrated in FIG. 8. The number of animals analyzed in each experimental group was 3, and severity of degenerative arthritis was evaluated on a scale of 0 to 5. From the results, a bar graph was prepared. Mean with SEM was indicated by an error bar. Virus particle doses A, B, C, and D were $1.25\times10^9$, $2.5\times10^9$, $5\times10^9$, and $1\times10^{10}$, respectively, in this increasing order.

As shown in FIG. 8, in the case of the control in which the empty vector AAV is intra-articularly injected, a high score of 4.5 to 5 was evaluated regardless of the amount of viral particles administered. In addition, in the comparison group in which AAV expressing the full-length Nkx3.2 (1-333) is intra-articularly injected, a low score of 1.5 was evaluated only in the AAV-administered group at $1\times10^{10}$. On the contrary, in the case of the experimental group in which AAV expressing the NKx3.2 fragment (123-320) is intra-articularly injected, an extremely low score of 1 or less was evaluated starting from the AAV-administered group at $1.25\times10^9$, which is the lowest dose. Namely, the Nkx3.2 fragment (123-320) is identified to have superior therapeutic efficacy against degenerative arthritis, compared with the full-length Nkx3.2 (1-333).

What is claimed is:

1. A vector comprising a polynucleotide encoding a polypeptide consisting of the following Formula (I):

N-terminal extension domain-core domain-C-terminal extension domain (I)

wherein the core domain is a polypeptide having the amino acid sequence of SEQ ID NO: 1;

the N-terminal extension domain is a polypeptide having the amino acid sequence of SEQ ID NO: 3 in which 1 to 42 amino acid residues are consecutively deletable from the N-terminus to the C-terminal direction, starting from the amino acid residue at position 1 of SEQ ID NO: 3; and the C-terminal extension domain is a polypeptide having the amino acid sequence of SEQ ID NO: 5 in which 1 to 23 amino acid residues are consecutively deletable from the C-terminus to the N-terminal direction, starting from the amino acid residue at position 24 of SEQ ID NO: 5.

2. A pharmaceutical composition comprising the vector of claim 1 and a pharmaceutically acceptable carrier.

3. A recombinant virus comprising the polynucleotide according to claim 1.

4. A host cell infected with the recombinant virus of claim 3.

5. A pharmaceutical composition comprising the recombinant virus of claim 3 and a pharmaceutically acceptable carrier.

6. The recombinant virus according to claim 3, wherein the virus is selected from the group consisting of an adenovirus, an adeno-associated virus (AAV), a retrovirus, a lentivirus, a herpes simplex virus, and a vaccinia virus.

7. A vector comprising a polynucleotide encoding a polypeptide selected from the group consisting of SEQ ID NO: 21, 13, 14, 20, 22, 23, 24, 25, 26, 27, or 28.

8. A pharmaceutical composition comprising the vector of claim 7 and a pharmaceutically acceptable carrier.

9. A recombinant virus comprising the polynucleotide according to claim 7.

10. A pharmaceutical composition comprising the recombinant virus of claim 9 and a pharmaceutically acceptable carrier.

11. A host cell infected with the recombinant virus of claim 9.

12. The recombinant virus according to claim 9, wherein the virus is selected from the group consisting of an adenovirus, an adeno-associated virus (AAV), a retrovirus, a lentivirus, a herpes simplex virus, and a vaccinia virus.

13. A vector comprising a polynucleotide encoding a polypeptide consisting of SEQ ID NO: 12 or 17.

14. A pharmaceutical composition comprising the vector of claim 13 and a pharmaceutically acceptable carrier.

15. A recombinant virus comprising the polynucleotide according to claim 13.

16. A pharmaceutical composition comprising the recombinant virus of claim 15 and a pharmaceutically acceptable carrier.

17. A host cell infected with the recombinant virus of claim 15.

18. The recombinant virus according to claim 15, wherein the virus is selected from the group consisting of an adenovirus, an adeno-associated virus (AAV), a retrovirus, a lentivirus, a herpes simplex virus, and a vaccinia virus.

* * * * *

SEQUENCE LISTING

<160> NUMBER OF SEQ ID NOS: 42

<210> SEQ ID NO 1
<211> LENGTH: 144
<212> TYPE: PRT
<213> ORGANISM: Artificial Sequence
<220> FEATURE:
<223> OTHER INFORMATION: 166-309 aa fragment of Nkx3.2

<400> SEQUENCE: 1

```
Gly Val Gly Pro Arg Gly Ala His Val Ser Ala Leu Cys Ser Gly Ala
1               5                  10                  15

Gly Gly Gly Gly Gly Ser Gly Pro Ala Gly Val Ala Glu Glu Glu Glu
            20                  25                  30

Glu Pro Ala Ala Pro Lys Pro Arg Lys Lys Arg Ser Arg Ala Ala Phe
        35                  40                  45

Ser His Ala Gln Val Phe Glu Leu Glu Arg Arg Phe Asn His Gln Arg
    50                  55                  60

Tyr Leu Ser Gly Pro Glu Arg Ala Asp Leu Ala Ala Ser Leu Lys Leu
65                  70                  75                  80

Thr Glu Thr Gln Val Lys Ile Trp Phe Gln Asn Arg Arg Tyr Lys Thr
                85                  90                  95

Lys Arg Arg Gln Met Ala Ala Asp Leu Leu Ala Ser Ala Pro Ala Ala
            100                 105                 110

Lys Lys Val Ala Val Lys Val Leu Val Arg Asp Asp Gln Arg Gln Tyr
        115                 120                 125

Leu Pro Gly Glu Val Leu Arg Pro Pro Ser Leu Leu Pro Leu Gln Pro
    130                 135                 140
```

<210> SEQ ID NO 2
<211> LENGTH: 432
<212> TYPE: DNA
<213> ORGANISM: Artificial Sequence
<220> FEATURE:
<223> OTHER INFORMATION: nucleotide sequence encoding 166-309 aa
      fragment of Nkx3.2

<400> SEQUENCE: 2

```
ggtgttggcc ccagaggtgc acacgtgtcc gcgctgtgca gcggggccgg cggcggggc       60 ggcagcgggc cggcaggcgt cgcggaggag gaggaggagc cggcggcgcc caagccacgc     120
```

```
aagaagcgct cgcgggccgc tttctcccac gcgcaggtct tcgagctgga gcgccgcttt    180
aaccaccagc gctacctgtc cgggcccgag cgcgcagacc tggccgcgtc gctgaagctc    240
accgagacgc aggtgaaaat ctggttccag aaccgtcgct acaagacaaa gcgccggcag    300
atggcagccg acctgctggc ctcggcgccc gccgccaaga aggtggccgt aaaggtgctg    360
gtgcgcgacg accagagaca atacctgccc ggcgaagtgc tgcggccacc ctcgcttctg    420
ccactgcagc cc                                                        432

<210> SEQ ID NO 3
<211> LENGTH: 43
<212> TYPE: PRT
<213> ORGANISM: Artificial Sequence
<220> FEATURE:
<223> OTHER INFORMATION: 123-165 aa fragment of Nkx3.2

<400> SEQUENCE: 3

Leu Ser Leu Gly Gln Pro Val Cys Glu Leu Ala Ala Ser Lys Asp Leu
1               5                   10                  15

Glu Glu Glu Ala Ala Gly Arg Ser Asp Ser Glu Met Ser Ala Ser Val
                20                  25                  30

Ser Gly Asp Arg Ser Pro Arg Thr Glu Asp Asp
        35                  40

<210> SEQ ID NO 4
<211> LENGTH: 129
<212> TYPE: DNA
<213> ORGANISM: Artificial Sequence
<220> FEATURE:
<223> OTHER INFORMATION: nucleotide sequence encoding 123-165 aa
      fragment of Nkx3.2

<400> SEQUENCE: 4
ttgagcctcg gccagccggt ctgtgagctg gccgcttcca agacctaga ggaggaagcc     60 gcgggccgga gcgacagcga gatgtccgcc agcgtctcag gcgaccgcag cccaaggacc    120
gaggacgac                                                           129

<210> SEQ ID NO 5
<211> LENGTH: 24
<212> TYPE: PRT
<213> ORGANISM: Artificial Sequence
<220> FEATURE:
<223> OTHER INFORMATION: 310-333 aa fragment encoding Nkx3.2

<400> SEQUENCE: 5

Ser Tyr Tyr Tyr Pro Tyr Tyr Cys Leu Pro Gly Trp Ala Leu Ser Thr
1               5                   10                  15

Cys Ala Ala Ala Ala Gly Thr Gln
                20

<210> SEQ ID NO 6
<211> LENGTH: 72
<212> TYPE: DNA
<213> ORGANISM: Artificial Sequence
<220> FEATURE:
<223> OTHER INFORMATION: nucleotide sequence encoding 310-333 aa
      fragment of Nkx3.2

<400> SEQUENCE: 6
tcctactatt acccgtacta ctgcctccca ggctgggcgc tctccacctg cgcagctgcc    60
gcaggcaccc ag                                                        72
```

<210> SEQ ID NO 7
<211> LENGTH: 333
<212> TYPE: PRT
<213> ORGANISM: Homo sapiens

<400> SEQUENCE: 7

Met Ala Val Arg Gly Ala Asn Thr Leu Thr Ser Phe Ser Ile Gln Ala
1               5                   10                  15

Ile Leu Asn Lys Lys Glu Glu Arg Gly Gly Leu Ala Ala Pro Glu Gly
            20                  25                  30

Arg Pro Ala Pro Gly Gly Thr Ala Ala Ser Val Ala Ala Pro Ala
        35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80

Ala Gly Arg Thr Ala Glu Ser Pro Glu Gly Trp Asp Ser Asp Ser Ala
                85                  90                  95

Leu Ser Glu Glu Asn Glu Ser Arg Arg Cys Ala Asp Ala Arg Gly
            100                 105                 110

Ala Ser Gly Ala Gly Leu Ala Gly Gly Ser Leu Ser Leu Gly Gln Pro
            115                 120                 125

Val Cys Glu Leu Ala Ala Ser Lys Asp Leu Glu Glu Ala Ala Gly
    130                 135                 140

Arg Ser Asp Ser Glu Met Ser Ala Ser Val Ser Gly Asp Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190

Ala Glu Glu Glu Glu Glu Pro Ala Ala Pro Lys Pro Arg Lys Lys Arg
            195                 200                 205

Ser Arg Ala Ala Phe Ser His Ala Gln Val Phe Glu Leu Glu Arg Arg
    210                 215                 220

Phe Asn His Gln Arg Tyr Leu Ser Gly Pro Glu Arg Ala Asp Leu Ala
225                 230                 235                 240

Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
            260                 265                 270

Ser Ala Pro Ala Ala Lys Lys Val Ala Val Lys Val Leu Val Arg Asp
    275                 280                 285

Asp Gln Arg Gln Tyr Leu Pro Gly Glu Val Leu Arg Pro Pro Ser Leu
290                 295                 300

Leu Pro Leu Gln Pro Ser Tyr Tyr Tyr Pro Tyr Tyr Cys Leu Pro Gly
305                 310                 315                 320

Trp Ala Leu Ser Thr Cys Ala Ala Ala Gly Thr Gln
                325                 330

<210> SEQ ID NO 8
<211> LENGTH: 1002
<212> TYPE: DNA
<213> ORGANISM: Homo sapiens

<400> SEQUENCE: 8

-continued

| | |
|---|---|
| atggctgtgc gcggcgccaa caccttgacg tccttctcca tccaggcgat cctcaacaag | 60 |
| aaagaggagc gcggcgggct ggccgcgcca gaggggcgcc cggcgcccgg gggcacagcg | 120 |
| gcatcggtgg ccgcggctcc cgctgtctgc tgttggcggc tctttgggga gagggacgcg | 180 |
| ggcgcgttgg ggggcgccga ggactctctg ctggcgtctc ctgccggtac cagaacagct | 240 |
| gcggggcgga ctgcggagag cccggaaggc tgggactcgg actccgcgct cagcgaggag | 300 |
| aacgagagca ggcggcgctg cgcggacgcg cgggggggcca gcggggccgg ccttgcgggg | 360 |
| ggatccttga gcctcggcca gccggtctgt gagctggccg cttccaaaga cctagaggag | 420 |
| gaagccgcgg gccggagcga cagcgagatg tccgccagcg tctcaggcga ccgcagccca | 480 |
| aggaccgagg acgacggtgt tggccccaga ggtgcacacg tgtccgcgct gtgcagcggg | 540 |
| gccggcggcg ggggcggcag cgggccggca ggcgtcgcgg aggaggagga ggagccggcg | 600 |
| gcgcccaagc cacgcaagaa gcgctcgcgg gccgctttct cccacgcgca ggtcttcgag | 660 |
| ctggagcgcc gctttaacca ccagcgctac ctgtccgggc ccgagcgcgc agacctggcc | 720 |
| gcgtcgctga agctcaccga gacgcaggtg aaaatctggt tccagaaccg tcgctacaag | 780 |
| acaaagcgcc ggcagatggc agccgacctg ctggcctcgg cgcccgccgc caagaaggtg | 840 |
| gccgtaaagg tgctggtgcg cgacgaccag agacaatacc tgcccggcga agtgctgcgg | 900 |
| ccacccctcg cttctgccact gcagccctcc tactattacc cgtactactg cctcccaggc | 960 |
| tgggcgctct ccacctgcgc agctgccgca ggcacccagt ga | 1002 |

<210> SEQ ID NO 9
<211> LENGTH: 320
<212> TYPE: PRT
<213> ORGANISM: Artificial Sequence
<220> FEATURE:
<223> OTHER INFORMATION: 1-320 aa fragment of Nkx3.2

<400> SEQUENCE: 9

```
Met Ala Val Arg Gly Ala Asn Thr Leu Thr Ser Phe Ser Ile Gln Ala
1               5                   10                  15

Ile Leu Asn Lys Lys Glu Glu Arg Gly Gly Leu Ala Ala Pro Glu Gly
            20                  25                  30

Arg Pro Ala Pro Gly Gly Thr Ala Ala Ser Val Ala Ala Ala Pro Ala
        35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80

Ala Gly Arg Thr Ala Glu Ser Pro Glu Gly Trp Asp Ser Asp Ser Ala
                85                  90                  95

Leu Ser Glu Glu Asn Glu Ser Arg Arg Arg Cys Ala Asp Ala Arg Gly
            100                 105                 110

Ala Ser Gly Ala Gly Leu Ala Gly Gly Ser Leu Ser Leu Gly Gln Pro
        115                 120                 125

Val Cys Glu Leu Ala Ala Ser Lys Asp Leu Glu Glu Ala Ala Gly
    130                 135                 140

Arg Ser Asp Ser Glu Met Ser Ala Ser Val Ser Gly Asp Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190
```

```
Ala Glu Glu Glu Glu Glu Pro Ala Ala Pro Lys Pro Arg Lys Lys Arg
            195                 200                 205

Ser Arg Ala Ala Phe Ser His Ala Gln Val Phe Glu Leu Glu Arg Arg
    210                 215                 220

Phe Asn His Gln Arg Tyr Leu Ser Gly Pro Glu Arg Ala Asp Leu Ala
225                 230                 235                 240

Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
            260                 265                 270

Ser Ala Pro Ala Ala Lys Lys Val Ala Val Lys Val Leu Val Arg Asp
                275                 280                 285

Asp Gln Arg Gln Tyr Leu Pro Gly Glu Val Leu Arg Pro Pro Ser Leu
290                 295                 300

Leu Pro Leu Gln Pro Ser Tyr Tyr Pro Tyr Tyr Cys Leu Pro Gly
305                 310                 315                 320

<210> SEQ ID NO 10
<211> LENGTH: 307
<212> TYPE: PRT
<213> ORGANISM: Artificial Sequence
<220> FEATURE:
<223> OTHER INFORMATION: 1-307 aa fragment of Nkx3.2

<400> SEQUENCE: 10

Met Ala Val Arg Gly Ala Asn Thr Leu Thr Ser Phe Ser Ile Gln Ala
1               5                   10                  15

Ile Leu Asn Lys Lys Glu Glu Arg Gly Gly Leu Ala Ala Pro Glu Gly
            20                  25                  30

Arg Pro Ala Pro Gly Gly Thr Ala Ala Ser Val Ala Ala Ala Pro Ala
            35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80

Ala Gly Arg Thr Ala Glu Ser Pro Glu Gly Trp Asp Ser Asp Ser Ala
                85                  90                  95

Leu Ser Glu Glu Asn Glu Ser Arg Arg Cys Ala Asp Ala Arg Gly
            100                 105                 110

Ala Ser Gly Ala Gly Leu Ala Gly Gly Ser Leu Ser Leu Gly Gln Pro
        115                 120                 125

Val Cys Glu Leu Ala Ala Ser Lys Asp Leu Glu Glu Ala Ala Gly
    130                 135                 140

Arg Ser Asp Ser Glu Met Ser Ala Ser Val Ser Gly Asp Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190

Ala Glu Glu Glu Glu Glu Pro Ala Ala Pro Lys Pro Arg Lys Lys Arg
        195                 200                 205

Ser Arg Ala Ala Phe Ser His Ala Gln Val Phe Glu Leu Glu Arg Arg
    210                 215                 220

Phe Asn His Gln Arg Tyr Leu Ser Gly Pro Glu Arg Ala Asp Leu Ala
225                 230                 235                 240
```

```
Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
            260                 265                 270

Ser Ala Pro Ala Ala Lys Lys Val Ala Val Lys Val Leu Val Arg Asp
        275                 280                 285

Asp Gln Arg Gln Tyr Leu Pro Gly Glu Val Leu Arg Pro Pro Ser Leu
    290                 295                 300

Leu Pro Leu
305

<210> SEQ ID NO 11
<211> LENGTH: 292
<212> TYPE: PRT
<213> ORGANISM: Artificial Sequence
<220> FEATURE:
<223> OTHER INFORMATION: 42-333 aa fragment of Nkx3.2

<400> SEQUENCE: 11

Ser Val Ala Ala Ala Pro Ala Val Cys Cys Trp Arg Leu Phe Gly Glu
1               5                   10                  15

Arg Asp Ala Gly Ala Leu Gly Gly Ala Glu Asp Ser Leu Leu Ala Ser
            20                  25                  30

Pro Ala Gly Thr Arg Thr Ala Ala Gly Arg Thr Ala Glu Ser Pro Glu
        35                  40                  45

Gly Trp Asp Ser Asp Ser Ala Leu Ser Glu Glu Asn Glu Ser Arg Arg
    50                  55                  60

Arg Cys Ala Asp Ala Arg Gly Ala Ser Gly Ala Gly Leu Ala Gly Gly
65                  70                  75                  80

Ser Leu Ser Leu Gly Gln Pro Val Cys Glu Leu Ala Ala Ser Lys Asp
                85                  90                  95

Leu Glu Glu Glu Ala Ala Gly Arg Ser Asp Ser Glu Met Ser Ala Ser
            100                 105                 110

Val Ser Gly Asp Arg Ser Pro Arg Thr Glu Asp Asp Gly Val Gly Pro
        115                 120                 125

Arg Gly Ala His Val Ser Ala Leu Cys Ser Gly Ala Gly Gly Gly Gly
    130                 135                 140

Gly Ser Gly Pro Ala Gly Val Ala Glu Glu Glu Glu Pro Ala Ala
145                 150                 155                 160

Pro Lys Pro Arg Lys Lys Arg Ser Arg Ala Ala Phe Ser His Ala Gln
                165                 170                 175

Val Phe Glu Leu Glu Arg Arg Phe Asn His Gln Arg Tyr Leu Ser Gly
            180                 185                 190

Pro Glu Arg Ala Asp Leu Ala Ala Ser Leu Lys Leu Thr Glu Thr Gln
        195                 200                 205

Val Lys Ile Trp Phe Gln Asn Arg Arg Tyr Lys Thr Lys Arg Arg Gln
    210                 215                 220

Met Ala Ala Asp Leu Leu Ala Ser Ala Pro Ala Ala Lys Lys Val Ala
225                 230                 235                 240

Val Lys Val Leu Val Arg Asp Asp Gln Arg Gln Tyr Leu Pro Gly Glu
                245                 250                 255

Val Leu Arg Pro Pro Ser Leu Leu Pro Leu Gln Pro Ser Tyr Tyr Tyr
            260                 265                 270

Pro Tyr Tyr Cys Leu Pro Gly Trp Ala Leu Ser Thr Cys Ala Ala Ala
        275                 280                 285
```

Ala Gly Thr Gln
    290

<210> SEQ ID NO 12
<211> LENGTH: 235
<212> TYPE: PRT
<213> ORGANISM: Artificial Sequence
<220> FEATURE:
<223> OTHER INFORMATION: 99-333 aa fragment of Nkx3.2

<400> SEQUENCE: 12

Glu Glu Asn Glu Ser Arg Arg Cys Ala Asp Ala Arg Gly Ala Ser
1               5                   10                  15

Gly Ala Gly Leu Ala Gly Gly Ser Leu Ser Leu Gly Gln Pro Val Cys
                20                  25                  30

Glu Leu Ala Ala Ser Lys Asp Leu Glu Glu Ala Ala Gly Arg Ser
                35                  40                  45

Asp Ser Glu Met Ser Ala Ser Val Ser Gly Asp Arg Ser Pro Arg Thr
        50                  55                  60

Glu Asp Asp Gly Val Gly Pro Arg Gly Ala His Val Ser Ala Leu Cys
65                  70                  75                  80

Ser Gly Ala Gly Gly Gly Gly Ser Gly Pro Ala Gly Val Ala Glu
                85                  90                  95

Glu Glu Glu Glu Pro Ala Ala Pro Lys Pro Arg Lys Lys Arg Ser Arg
                100                 105                 110

Ala Ala Phe Ser His Ala Gln Val Phe Glu Leu Glu Arg Arg Phe Asn
                115                 120                 125

His Gln Arg Tyr Leu Ser Gly Pro Glu Arg Ala Asp Leu Ala Ala Ser
        130                 135                 140

Leu Lys Leu Thr Glu Thr Gln Val Lys Ile Trp Phe Gln Asn Arg Arg
145                 150                 155                 160

Tyr Lys Thr Lys Arg Arg Gln Met Ala Ala Asp Leu Leu Ala Ser Ala
                165                 170                 175

Pro Ala Ala Lys Lys Val Ala Val Lys Val Leu Val Arg Asp Asp Gln
                180                 185                 190

Arg Gln Tyr Leu Pro Gly Glu Val Leu Arg Pro Pro Ser Leu Leu Pro
        195                 200                 205

Leu Gln Pro Ser Tyr Tyr Tyr Pro Tyr Tyr Cys Leu Pro Gly Trp Ala
        210                 215                 220

Leu Ser Thr Cys Ala Ala Ala Gly Thr Gln
225                 230                 235

<210> SEQ ID NO 13
<211> LENGTH: 222
<212> TYPE: PRT
<213> ORGANISM: Artificial Sequence
<220> FEATURE:
<223> OTHER INFORMATION: 112-333 aa fragment of Nkx3.2

<400> SEQUENCE: 13

Gly Ala Ser Gly Ala Gly Leu Ala Gly Gly Ser Leu Ser Leu Gly Gln
1               5                   10                  15

Pro Val Cys Glu Leu Ala Ala Ser Lys Asp Leu Glu Glu Ala Ala
                20                  25                  30

Gly Arg Ser Asp Ser Glu Met Ser Ala Ser Val Ser Gly Asp Arg Ser
        35                  40                  45

Pro Arg Thr Glu Asp Asp Gly Val Gly Pro Arg Gly Ala His Val Ser

```
Ala Leu Cys Ser Gly Ala Gly Gly Gly Ser Gly Pro Ala Gly
65                  70                  75                  80

Val Ala Glu Glu Glu Glu Pro Ala Ala Pro Lys Pro Arg Lys Lys
                85                  90                  95

Arg Ser Arg Ala Ala Phe Ser His Ala Gln Val Phe Glu Leu Glu Arg
            100                 105                 110

Arg Phe Asn His Gln Arg Tyr Leu Ser Gly Pro Glu Arg Ala Asp Leu
            115                 120                 125

Ala Ala Ser Leu Lys Leu Thr Glu Thr Gln Val Lys Ile Trp Phe Gln
    130                 135                 140

Asn Arg Arg Tyr Lys Thr Lys Arg Arg Gln Met Ala Ala Asp Leu Leu
145                 150                 155                 160

Ala Ser Ala Pro Ala Ala Lys Lys Val Ala Val Lys Val Leu Val Arg
                165                 170                 175

Asp Asp Gln Arg Gln Tyr Leu Pro Gly Glu Val Leu Arg Pro Pro Ser
            180                 185                 190

Leu Leu Pro Leu Gln Pro Ser Tyr Tyr Tyr Pro Tyr Tyr Cys Leu Pro
        195                 200                 205

Gly Trp Ala Leu Ser Thr Cys Ala Ala Ala Gly Thr Gln
    210                 215                 220

<210> SEQ ID NO 14
<211> LENGTH: 211
<212> TYPE: PRT
<213> ORGANISM: Artificial Sequence
<220> FEATURE:
<223> OTHER INFORMATION: 123-333 aa fragment of Nkx3.2

<400> SEQUENCE: 14

Leu Ser Leu Gly Gln Pro Val Cys Glu Leu Ala Ala Ser Lys Asp Leu
1               5                   10                  15

Glu Glu Glu Ala Ala Gly Arg Ser Asp Ser Glu Met Ser Ala Ser Val
            20                  25                  30

Ser Gly Asp Arg Ser Pro Arg Thr Glu Asp Asp Gly Val Gly Pro Arg
        35                  40                  45

Gly Ala His Val Ser Ala Leu Cys Ser Gly Ala Gly Gly Gly Gly
    50                  55                  60

Ser Gly Pro Ala Gly Val Ala Glu Glu Glu Glu Pro Ala Ala Pro
65                  70                  75                  80

Lys Pro Arg Lys Lys Arg Ser Arg Ala Ala Phe Ser His Ala Gln Val
                85                  90                  95

Phe Glu Leu Glu Arg Arg Phe Asn His Gln Arg Tyr Leu Ser Gly Pro
            100                 105                 110

Glu Arg Ala Asp Leu Ala Ala Ser Leu Lys Leu Thr Glu Thr Gln Val
        115                 120                 125

Lys Ile Trp Phe Gln Asn Arg Arg Tyr Lys Thr Lys Arg Arg Gln Met
    130                 135                 140

Ala Ala Asp Leu Leu Ala Ser Ala Pro Ala Ala Lys Lys Val Ala Val
145                 150                 155                 160

Lys Val Leu Val Arg Asp Asp Gln Arg Gln Tyr Leu Pro Gly Glu Val
                165                 170                 175

Leu Arg Pro Pro Ser Leu Leu Pro Leu Gln Pro Ser Tyr Tyr Tyr Pro
            180                 185                 190

Tyr Tyr Cys Leu Pro Gly Trp Ala Leu Ser Thr Cys Ala Ala Ala Ala
```

```
                    195                 200                 205
Gly Thr Gln
    210

<210> SEQ ID NO 15
<211> LENGTH: 232
<212> TYPE: PRT
<213> ORGANISM: Artificial Sequence
<220> FEATURE:
<223> OTHER INFORMATION: 99-330 aa fragment of Nkx3.2

<400> SEQUENCE: 15

Glu Glu Asn Glu Ser Arg Arg Arg Cys Ala Asp Ala Arg Gly Ala Ser
1               5                   10                  15

Gly Ala Gly Leu Ala Gly Gly Ser Leu Ser Leu Gly Gln Pro Val Cys
            20                  25                  30

Glu Leu Ala Ala Ser Lys Asp Leu Glu Glu Glu Ala Ala Gly Arg Ser
        35                  40                  45

Asp Ser Glu Met Ser Ala Ser Val Ser Gly Asp Arg Ser Pro Arg Thr
    50                  55                  60

Glu Asp Asp Gly Val Gly Pro Arg Gly Ala His Val Ser Ala Leu Cys
65                  70                  75                  80

Ser Gly Ala Gly Gly Gly Gly Ser Gly Pro Ala Gly Val Ala Glu
                85                  90                  95

Glu Glu Glu Glu Pro Ala Ala Pro Lys Pro Arg Lys Lys Arg Ser Arg
            100                 105                 110

Ala Ala Phe Ser His Ala Gln Val Phe Glu Leu Glu Arg Arg Phe Asn
        115                 120                 125

His Gln Arg Tyr Leu Ser Gly Pro Glu Arg Ala Asp Leu Ala Ala Ser
    130                 135                 140

Leu Lys Leu Thr Glu Thr Gln Val Lys Ile Trp Phe Gln Asn Arg Arg
145                 150                 155                 160

Tyr Lys Thr Lys Arg Arg Gln Met Ala Ala Asp Leu Leu Ala Ser Ala
                165                 170                 175

Pro Ala Ala Lys Lys Val Ala Val Lys Val Leu Val Arg Asp Asp Gln
            180                 185                 190

Arg Gln Tyr Leu Pro Gly Glu Val Leu Arg Pro Pro Ser Leu Leu Pro
        195                 200                 205

Leu Gln Pro Ser Tyr Tyr Tyr Pro Tyr Tyr Cys Leu Pro Gly Trp Ala
    210                 215                 220

Leu Ser Thr Cys Ala Ala Ala Ala
225                 230

<210> SEQ ID NO 16
<211> LENGTH: 229
<212> TYPE: PRT
<213> ORGANISM: Artificial Sequence
<220> FEATURE:
<223> OTHER INFORMATION: 99-327 aa fragment of Nkx3.2

<400> SEQUENCE: 16

Glu Glu Asn Glu Ser Arg Arg Arg Cys Ala Asp Ala Arg Gly Ala Ser
1               5                   10                  15

Gly Ala Gly Leu Ala Gly Gly Ser Leu Ser Leu Gly Gln Pro Val Cys
            20                  25                  30

Glu Leu Ala Ala Ser Lys Asp Leu Glu Glu Glu Ala Ala Gly Arg Ser
        35                  40                  45
```

```
Asp Ser Glu Met Ser Ala Ser Val Ser Gly Asp Arg Ser Pro Arg Thr
 50                  55                  60
Glu Asp Asp Gly Val Gly Pro Arg Gly Ala His Val Ser Ala Leu Cys
 65                  70                  75                  80
Ser Gly Ala Gly Gly Gly Gly Ser Gly Pro Ala Gly Val Ala Glu
                 85                  90                  95
Glu Glu Glu Glu Pro Ala Ala Pro Lys Pro Arg Lys Lys Arg Ser Arg
                100                 105                 110
Ala Ala Phe Ser His Ala Gln Val Phe Glu Leu Glu Arg Arg Phe Asn
            115                 120                 125
His Gln Arg Tyr Leu Ser Gly Pro Glu Arg Ala Asp Leu Ala Ala Ser
130                 135                 140
Leu Lys Leu Thr Glu Thr Gln Val Lys Ile Trp Phe Gln Asn Arg Arg
145                 150                 155                 160
Tyr Lys Thr Lys Arg Arg Gln Met Ala Ala Asp Leu Leu Ala Ser Ala
                165                 170                 175
Pro Ala Ala Lys Lys Val Ala Val Lys Val Leu Val Arg Asp Asp Gln
                180                 185                 190
Arg Gln Tyr Leu Pro Gly Glu Val Leu Arg Pro Pro Ser Leu Leu Pro
            195                 200                 205
Leu Gln Pro Ser Tyr Tyr Tyr Pro Tyr Tyr Cys Leu Pro Gly Trp Ala
210                 215                 220
Leu Ser Thr Cys Ala
225

<210> SEQ ID NO 17
<211> LENGTH: 222
<212> TYPE: PRT
<213> ORGANISM: Artificial Sequence
<220> FEATURE:
<223> OTHER INFORMATION: 99-320 aa fragment of Nkx3.2

<400> SEQUENCE: 17

Glu Glu Asn Glu Ser Arg Arg Arg Cys Ala Asp Ala Arg Gly Ala Ser
1                   5                  10                  15
Gly Ala Gly Leu Ala Gly Gly Ser Leu Ser Leu Gly Gln Pro Val Cys
                 20                  25                  30
Glu Leu Ala Ala Ser Lys Asp Leu Glu Glu Glu Ala Ala Gly Arg Ser
             35                  40                  45
Asp Ser Glu Met Ser Ala Ser Val Ser Gly Asp Arg Ser Pro Arg Thr
 50                  55                  60
Glu Asp Asp Gly Val Gly Pro Arg Gly Ala His Val Ser Ala Leu Cys
 65                  70                  75                  80
Ser Gly Ala Gly Gly Gly Gly Ser Gly Pro Ala Gly Val Ala Glu
                 85                  90                  95
Glu Glu Glu Glu Pro Ala Ala Pro Lys Pro Arg Lys Lys Arg Ser Arg
                100                 105                 110
Ala Ala Phe Ser His Ala Gln Val Phe Glu Leu Glu Arg Arg Phe Asn
            115                 120                 125
His Gln Arg Tyr Leu Ser Gly Pro Glu Arg Ala Asp Leu Ala Ala Ser
130                 135                 140
Leu Lys Leu Thr Glu Thr Gln Val Lys Ile Trp Phe Gln Asn Arg Arg
145                 150                 155                 160
Tyr Lys Thr Lys Arg Arg Gln Met Ala Ala Asp Leu Leu Ala Ser Ala
                165                 170                 175
```

```
Pro Ala Ala Lys Lys Val Ala Val Lys Val Leu Val Arg Asp Asp Gln
            180                 185                 190

Arg Gln Tyr Leu Pro Gly Glu Val Leu Arg Pro Pro Ser Leu Leu Pro
        195                 200                 205

Leu Gln Pro Ser Tyr Tyr Tyr Pro Tyr Cys Leu Pro Gly
    210                 215                 220

<210> SEQ ID NO 18
<211> LENGTH: 223
<212> TYPE: PRT
<213> ORGANISM: Artificial Sequence
<220> FEATURE:
<223> OTHER INFORMATION: 105-327 aa fragment of Nkx3.2

<400> SEQUENCE: 18

Arg Arg Cys Ala Asp Ala Arg Gly Ala Ser Gly Ala Gly Leu Ala Gly
1               5                   10                  15

Gly Ser Leu Ser Leu Gly Gln Pro Val Cys Glu Leu Ala Ala Ser Lys
            20                  25                  30

Asp Leu Glu Glu Glu Ala Ala Gly Arg Ser Asp Ser Glu Met Ser Ala
        35                  40                  45

Ser Val Ser Gly Asp Arg Ser Pro Arg Thr Glu Asp Asp Gly Val Gly
    50                  55                  60

Pro Arg Gly Ala His Val Ser Ala Leu Cys Ser Gly Ala Gly Gly Gly
65                  70                  75                  80

Gly Gly Ser Gly Pro Ala Gly Val Ala Glu Glu Glu Glu Glu Pro Ala
                85                  90                  95

Ala Pro Lys Pro Arg Lys Lys Arg Ser Arg Ala Ala Phe Ser His Ala
            100                 105                 110

Gln Val Phe Glu Leu Glu Arg Arg Phe Asn His Gln Arg Tyr Leu Ser
        115                 120                 125

Gly Pro Glu Arg Ala Asp Leu Ala Ala Ser Leu Lys Leu Thr Glu Thr
    130                 135                 140

Gln Val Lys Ile Trp Phe Gln Asn Arg Arg Tyr Lys Thr Lys Arg Arg
145                 150                 155                 160

Gln Met Ala Ala Asp Leu Leu Ala Ser Ala Pro Ala Ala Lys Lys Val
                165                 170                 175

Ala Val Lys Val Leu Val Arg Asp Asp Gln Arg Gln Tyr Leu Pro Gly
            180                 185                 190

Glu Val Leu Arg Pro Pro Ser Leu Leu Pro Gln Pro Ser Tyr Tyr Tyr
        195                 200                 205

Tyr Pro Tyr Tyr Cys Leu Pro Gly Trp Ala Leu Ser Thr Cys Ala
    210                 215                 220

<210> SEQ ID NO 19
<211> LENGTH: 215
<212> TYPE: PRT
<213> ORGANISM: Artificial Sequence
<220> FEATURE:
<223> OTHER INFORMATION: 110-324 aa fragment of Nkx3.2

<400> SEQUENCE: 19

Ala Arg Gly Ala Ser Gly Ala Gly Leu Ala Gly Gly Ser Leu Ser Leu
1               5                   10                  15

Gly Gln Pro Val Cys Glu Leu Ala Ala Ser Lys Asp Leu Glu Glu Glu
            20                  25                  30

Ala Ala Gly Arg Ser Asp Ser Glu Met Ser Ala Ser Val Ser Gly Asp
        35                  40                  45
```

```
Arg Ser Pro Arg Thr Glu Asp Asp Gly Val Gly Pro Arg Gly Ala His
    50                  55                  60

Val Ser Ala Leu Cys Ser Gly Ala Gly Gly Gly Gly Ser Gly Pro
65                  70                  75                  80

Ala Gly Val Ala Glu Glu Glu Glu Pro Ala Ala Pro Lys Pro Arg
                85                  90                  95

Lys Lys Arg Ser Arg Ala Ala Phe Ser His Ala Gln Val Phe Glu Leu
                100                 105                 110

Glu Arg Arg Phe Asn His Gln Arg Tyr Leu Ser Gly Pro Glu Arg Ala
                115                 120                 125

Asp Leu Ala Ala Ser Leu Lys Leu Thr Glu Thr Gln Val Lys Ile Trp
    130                 135                 140

Phe Gln Asn Arg Arg Tyr Lys Thr Lys Arg Arg Gln Met Ala Ala Asp
145                 150                 155                 160

Leu Leu Ala Ser Ala Pro Ala Ala Lys Lys Val Ala Val Lys Val Leu
                165                 170                 175

Val Arg Asp Asp Gln Arg Gln Tyr Leu Pro Gly Glu Val Leu Arg Pro
                180                 185                 190

Pro Ser Leu Leu Pro Leu Gln Pro Ser Tyr Tyr Tyr Pro Tyr Tyr Cys
                195                 200                 205

Leu Pro Gly Trp Ala Leu Ser
    210                 215

<210> SEQ ID NO 20
<211> LENGTH: 209
<212> TYPE: PRT
<213> ORGANISM: Artificial Sequence
<220> FEATURE:
<223> OTHER INFORMATION: 112-320 aa fragment of Nkx3.2

<400> SEQUENCE: 20

Gly Ala Ser Gly Ala Gly Leu Ala Gly Gly Ser Leu Ser Leu Gly Gln
1               5                   10                  15

Pro Val Cys Glu Leu Ala Ala Ser Lys Asp Leu Glu Glu Glu Ala Ala
                20                  25                  30

Gly Arg Ser Asp Ser Glu Met Ser Ala Ser Val Ser Gly Asp Arg Ser
            35                  40                  45

Pro Arg Thr Glu Asp Asp Gly Val Gly Pro Arg Gly Ala His Val Ser
    50                  55                  60

Ala Leu Cys Ser Gly Ala Gly Gly Gly Gly Ser Gly Pro Ala Gly
65                  70                  75                  80

Val Ala Glu Glu Glu Glu Pro Ala Ala Pro Lys Pro Arg Lys Lys
                85                  90                  95

Arg Ser Arg Ala Ala Phe Ser His Ala Gln Val Phe Glu Leu Glu Arg
                100                 105                 110

Arg Phe Asn His Gln Arg Tyr Leu Ser Gly Pro Glu Arg Ala Asp Leu
                115                 120                 125

Ala Ala Ser Leu Lys Leu Thr Glu Thr Gln Val Lys Ile Trp Phe Gln
    130                 135                 140

Asn Arg Arg Tyr Lys Thr Lys Arg Arg Gln Met Ala Ala Asp Leu Leu
145                 150                 155                 160

Ala Ser Ala Pro Ala Ala Lys Lys Val Ala Val Lys Val Leu Val Arg
                165                 170                 175

Asp Asp Gln Arg Gln Tyr Leu Pro Gly Glu Val Leu Arg Pro Pro Ser
                180                 185                 190
```

```
Leu Leu Pro Leu Gln Pro Ser Tyr Tyr Tyr Pro Tyr Tyr Cys Leu Pro
        195                 200                 205

Gly

<210> SEQ ID NO 21
<211> LENGTH: 198
<212> TYPE: PRT
<213> ORGANISM: Artificial Sequence
<220> FEATURE:
<223> OTHER INFORMATION: 123-320 aa fragment of Nkx3.2

<400> SEQUENCE: 21

Leu Ser Leu Gly Gln Pro Val Cys Glu Leu Ala Ala Ser Lys Asp Leu
1               5                   10                  15

Glu Glu Glu Ala Ala Gly Arg Ser Asp Ser Glu Met Ser Ala Ser Val
            20                  25                  30

Ser Gly Asp Arg Ser Pro Arg Thr Glu Asp Asp Gly Val Gly Pro Arg
        35                  40                  45

Gly Ala His Val Ser Ala Leu Cys Ser Gly Ala Gly Gly Gly Gly Gly
    50                  55                  60

Ser Gly Pro Ala Gly Val Ala Glu Glu Glu Glu Pro Ala Ala Pro
65                  70                  75                  80

Lys Pro Arg Lys Lys Arg Ser Arg Ala Ala Phe Ser His Ala Gln Val
                85                  90                  95

Phe Glu Leu Glu Arg Arg Phe Asn His Gln Arg Tyr Leu Ser Gly Pro
            100                 105                 110

Glu Arg Ala Asp Leu Ala Ala Ser Leu Lys Leu Thr Glu Thr Gln Val
        115                 120                 125

Lys Ile Trp Phe Gln Asn Arg Arg Tyr Lys Thr Lys Arg Arg Gln Met
    130                 135                 140

Ala Ala Asp Leu Leu Ala Ser Ala Pro Ala Ala Lys Lys Val Ala Val
145                 150                 155                 160

Lys Val Leu Val Arg Asp Asp Gln Arg Gln Tyr Leu Pro Gly Glu Val
                165                 170                 175

Leu Arg Pro Pro Ser Leu Leu Pro Leu Gln Pro Ser Tyr Tyr Tyr Pro
            180                 185                 190

Tyr Tyr Cys Leu Pro Gly
        195

<210> SEQ ID NO 22
<211> LENGTH: 191
<212> TYPE: PRT
<213> ORGANISM: Artificial Sequence
<220> FEATURE:
<223> OTHER INFORMATION: 130-320 aa fragment of Nkx3.2

<400> SEQUENCE: 22

Cys Glu Leu Ala Ala Ser Lys Asp Leu Glu Glu Glu Ala Ala Gly Arg
1               5                   10                  15

Ser Asp Ser Glu Met Ser Ala Ser Val Ser Gly Asp Arg Ser Pro Arg
            20                  25                  30

Thr Glu Asp Asp Gly Val Gly Pro Arg Gly Ala His Val Ser Ala Leu
        35                  40                  45

Cys Ser Gly Ala Gly Gly Gly Gly Ser Gly Pro Ala Gly Val Ala
    50                  55                  60

Glu Glu Glu Glu Pro Ala Ala Pro Lys Pro Arg Lys Lys Arg Ser
65                  70                  75                  80
```

```
Arg Ala Ala Phe Ser His Ala Gln Val Phe Glu Leu Glu Arg Arg Phe
                85                  90                  95

Asn His Gln Arg Tyr Leu Ser Gly Pro Glu Arg Ala Asp Leu Ala Ala
            100                 105                 110

Ser Leu Lys Leu Thr Glu Thr Gln Val Lys Ile Trp Phe Gln Asn Arg
        115                 120                 125

Arg Tyr Lys Thr Lys Arg Gln Met Ala Ala Asp Leu Leu Ala Ser
    130                 135                 140

Ala Pro Ala Ala Lys Lys Val Ala Val Lys Val Leu Val Arg Asp Asp
145                 150                 155                 160

Gln Arg Gln Tyr Leu Pro Gly Glu Val Leu Arg Pro Pro Ser Leu Leu
                165                 170                 175

Pro Leu Gln Pro Ser Tyr Tyr Tyr Pro Tyr Tyr Cys Leu Pro Gly
            180                 185                 190

<210> SEQ ID NO 23
<211> LENGTH: 171
<212> TYPE: PRT
<213> ORGANISM: Artificial Sequence
<220> FEATURE:
<223> OTHER INFORMATION: 150-320 aa fragment of Nkx3.2

<400> SEQUENCE: 23

Met Ser Ala Ser Val Ser Gly Asp Arg Ser Pro Arg Thr Glu Asp Asp
1               5                   10                  15

Gly Val Gly Pro Arg Gly Ala His Val Ser Ala Leu Cys Ser Gly Ala
            20                  25                  30

Gly Gly Gly Gly Ser Gly Pro Ala Gly Val Ala Glu Glu Glu Glu
        35                  40                  45

Glu Pro Ala Ala Pro Lys Pro Arg Lys Lys Arg Ser Arg Ala Ala Phe
 50                 55                  60

Ser His Ala Gln Val Phe Glu Leu Glu Arg Arg Phe Asn His Gln Arg
65                  70                  75                  80

Tyr Leu Ser Gly Pro Glu Arg Ala Asp Leu Ala Ala Ser Leu Lys Leu
                85                  90                  95

Thr Glu Thr Gln Val Lys Ile Trp Phe Gln Asn Arg Arg Tyr Lys Thr
            100                 105                 110

Lys Arg Arg Gln Met Ala Ala Asp Leu Leu Ala Ser Ala Pro Ala Ala
        115                 120                 125

Lys Lys Val Ala Val Lys Val Leu Val Arg Asp Asp Gln Arg Gln Tyr
    130                 135                 140

Leu Pro Gly Glu Val Leu Arg Pro Pro Ser Leu Leu Pro Leu Gln Pro
145                 150                 155                 160

Ser Tyr Tyr Tyr Pro Tyr Tyr Cys Leu Pro Gly
                165                 170

<210> SEQ ID NO 24
<211> LENGTH: 166
<212> TYPE: PRT
<213> ORGANISM: Artificial Sequence
<220> FEATURE:
<223> OTHER INFORMATION: 153-318 aa fragment of Nkx3.2

<400> SEQUENCE: 24

Ser Val Ser Gly Asp Arg Ser Pro Arg Thr Glu Asp Asp Gly Val Gly
1               5                   10                  15

Pro Arg Gly Ala His Val Ser Ala Leu Cys Ser Gly Ala Gly Gly Gly
```

```
                    20                  25                  30
Gly Gly Ser Gly Pro Ala Gly Val Ala Glu Glu Glu Glu Pro Ala
            35                  40                  45

Ala Pro Lys Pro Arg Lys Lys Arg Ser Arg Ala Ala Phe Ser His Ala
    50                  55                  60

Gln Val Phe Glu Leu Glu Arg Arg Phe Asn His Gln Arg Tyr Leu Ser
65                  70                  75                  80

Gly Pro Glu Arg Ala Asp Leu Ala Ala Ser Leu Lys Leu Thr Glu Thr
                85                  90                  95

Gln Val Lys Ile Trp Phe Gln Asn Arg Arg Tyr Lys Thr Lys Arg Arg
            100                 105                 110

Gln Met Ala Ala Asp Leu Leu Ala Ser Ala Pro Ala Ala Lys Lys Val
        115                 120                 125

Ala Val Lys Val Leu Val Arg Asp Asp Gln Arg Gln Tyr Leu Pro Gly
    130                 135                 140

Glu Val Leu Arg Pro Pro Ser Leu Leu Pro Leu Gln Pro Ser Tyr Tyr
145                 150                 155                 160

Tyr Pro Tyr Tyr Cys Leu
                165

<210> SEQ ID NO 25
<211> LENGTH: 161
<212> TYPE: PRT
<213> ORGANISM: Artificial Sequence
<220> FEATURE:
<223> OTHER INFORMATION: 156-316 aa fragment of Nkx3.2

<400> SEQUENCE: 25

Gly Asp Arg Ser Pro Arg Thr Glu Asp Gly Val Gly Pro Arg Gly
1               5                   10                  15

Ala His Val Ser Ala Leu Cys Ser Gly Ala Gly Gly Gly Gly Ser
            20                  25                  30

Gly Pro Ala Gly Val Ala Glu Glu Glu Glu Pro Ala Ala Pro Lys
        35                  40                  45

Pro Arg Lys Lys Arg Ser Arg Ala Ala Phe Ser His Ala Gln Val Phe
    50                  55                  60

Glu Leu Glu Arg Arg Phe Asn His Gln Arg Tyr Leu Ser Gly Pro Glu
65                  70                  75                  80

Arg Ala Asp Leu Ala Ala Ser Leu Lys Leu Thr Glu Thr Gln Val Lys
                85                  90                  95

Ile Trp Phe Gln Asn Arg Arg Tyr Lys Thr Lys Arg Arg Gln Met Ala
            100                 105                 110

Ala Asp Leu Leu Ala Ser Ala Pro Ala Ala Lys Lys Val Ala Val Lys
        115                 120                 125

Val Leu Val Arg Asp Asp Gln Arg Gln Tyr Leu Pro Gly Glu Val Leu
    130                 135                 140

Arg Pro Pro Ser Leu Leu Pro Leu Gln Pro Ser Tyr Tyr Tyr Pro Tyr
145                 150                 155                 160

Tyr

<210> SEQ ID NO 26
<211> LENGTH: 156
<212> TYPE: PRT
<213> ORGANISM: Artificial Sequence
<220> FEATURE:
<223> OTHER INFORMATION: 159-314 aa fragment of Nkx3.2
```

```
<400> SEQUENCE: 26

Ser Pro Arg Thr Glu Asp Asp Gly Val Gly Pro Arg Gly Ala His Val
1               5                   10                  15

Ser Ala Leu Cys Ser Gly Ala Gly Gly Gly Gly Ser Gly Pro Ala
            20                  25                  30

Gly Val Ala Glu Glu Glu Glu Pro Ala Ala Pro Lys Pro Arg Lys
                35                  40                  45

Lys Arg Ser Arg Ala Ala Phe Ser His Ala Gln Val Phe Glu Leu Glu
    50                  55                  60

Arg Arg Phe Asn His Gln Arg Tyr Leu Ser Gly Pro Glu Arg Ala Asp
65              70                  75                  80

Leu Ala Ala Ser Leu Lys Leu Thr Glu Thr Gln Val Lys Ile Trp Phe
                85                  90                  95

Gln Asn Arg Arg Tyr Lys Thr Lys Arg Arg Gln Met Ala Ala Asp Leu
                100                 105                 110

Leu Ala Ser Ala Pro Ala Ala Lys Lys Val Ala Val Lys Val Leu Val
            115                 120                 125

Arg Asp Asp Gln Arg Gln Tyr Leu Pro Gly Glu Val Leu Arg Pro Pro
130                 135                 140

Ser Leu Leu Pro Leu Gln Pro Ser Tyr Tyr Tyr Pro
145                 150                 155

<210> SEQ ID NO 27
<211> LENGTH: 151
<212> TYPE: PRT
<213> ORGANISM: Artificial Sequence
<220> FEATURE:
<223> OTHER INFORMATION: 162-312 polypeptide fragment of Nkx3.2

<400> SEQUENCE: 27

Thr Glu Asp Asp Gly Val Gly Pro Arg Gly Ala His Val Ser Ala Leu
1               5                   10                  15

Cys Ser Gly Ala Gly Gly Gly Gly Ser Gly Pro Ala Gly Val Ala
            20                  25                  30

Glu Glu Glu Glu Glu Pro Ala Ala Pro Lys Pro Arg Lys Lys Arg Ser
                35                  40                  45

Arg Ala Ala Phe Ser His Ala Gln Val Phe Glu Leu Glu Arg Arg Phe
    50                  55                  60

Asn His Gln Arg Tyr Leu Ser Gly Pro Glu Arg Ala Asp Leu Ala Ala
65              70                  75                  80

Ser Leu Lys Leu Thr Glu Thr Gln Val Lys Ile Trp Phe Gln Asn Arg
                85                  90                  95

Arg Tyr Lys Thr Lys Arg Arg Gln Met Ala Ala Asp Leu Leu Ala Ser
                100                 105                 110

Ala Pro Ala Ala Lys Lys Val Ala Val Lys Val Leu Val Arg Asp Asp
            115                 120                 125

Gln Arg Gln Tyr Leu Pro Gly Glu Val Leu Arg Pro Pro Ser Leu Leu
130                 135                 140

Pro Leu Gln Pro Ser Tyr Tyr
145                 150

<210> SEQ ID NO 28
<211> LENGTH: 146
<212> TYPE: PRT
<213> ORGANISM: Artificial Sequence
<220> FEATURE:
<223> OTHER INFORMATION: 165-310 polypeptide fragment of Nkx3.2
```

<400> SEQUENCE: 28

```
Asp Gly Val Gly Pro Arg Gly Ala His Val Ser Ala Leu Cys Ser Gly
1               5                   10                  15

Ala Gly Gly Gly Gly Ser Gly Pro Ala Gly Val Ala Glu Glu Glu
                20                  25                  30

Glu Glu Pro Ala Ala Pro Lys Pro Arg Lys Lys Arg Ser Arg Ala Ala
            35                  40                  45

Phe Ser His Ala Gln Val Phe Glu Leu Glu Arg Arg Phe Asn His Gln
        50                  55                  60

Arg Tyr Leu Ser Gly Pro Glu Arg Ala Asp Leu Ala Ala Ser Leu Lys
65                  70                  75                  80

Leu Thr Glu Thr Gln Val Lys Ile Trp Phe Gln Asn Arg Arg Tyr Lys
                85                  90                  95

Thr Lys Arg Arg Gln Met Ala Ala Asp Leu Leu Ala Ser Ala Pro Ala
            100                 105                 110

Ala Lys Lys Val Ala Val Lys Val Leu Val Arg Asp Asp Gln Arg Gln
        115                 120                 125

Tyr Leu Pro Gly Glu Val Leu Arg Pro Pro Ser Leu Leu Pro Leu Gln
130                 135                 140

Pro Ser
145
```

<210> SEQ ID NO 29
<211> LENGTH: 282
<212> TYPE: PRT
<213> ORGANISM: Homo sapiens

<400> SEQUENCE: 29

```
Met Ser Arg Gln Thr Ala Thr Ala Leu Pro Thr Gly Thr Ser Lys Cys
1               5                   10                  15

Pro Pro Ser Gln Arg Val Pro Ala Leu Thr Gly Thr Thr Ala Ser Asn
                20                  25                  30

Asn Asp Leu Ala Ser Leu Phe Glu Cys Pro Val Cys Phe Asp Tyr Val
            35                  40                  45

Leu Pro Pro Ile Leu Gln Cys Gln Ser Gly His Leu Val Cys Ser Asn
        50                  55                  60

Cys Arg Pro Lys Leu Thr Cys Cys Pro Thr Cys Arg Gly Pro Leu Gly
65                  70                  75                  80

Ser Ile Arg Asn Leu Ala Met Glu Lys Val Ala Asn Ser Val Leu Phe
                85                  90                  95

Pro Cys Lys Tyr Ala Ser Ser Gly Cys Glu Ile Thr Leu Pro His Thr
            100                 105                 110

Glu Lys Ala Asp His Glu Glu Leu Cys Glu Phe Arg Pro Tyr Ser Cys
        115                 120                 125

Pro Cys Pro Gly Ala Ser Cys Lys Trp Gln Gly Ser Leu Asp Ala Val
130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
            180                 185                 190

Leu Glu Lys Gln Glu Lys Tyr Asp Gly His Gln Gln Phe Phe Ala Ile
        195                 200                 205
```

Val Gln Leu Ile Gly Thr Arg Lys Gln Ala Glu Asn Phe Ala Tyr Arg
    210                 215                 220

Leu Glu Leu Asn Gly His Arg Arg Arg Leu Thr Trp Glu Ala Thr Pro
225                 230                 235                 240

Arg Ser Ile His Glu Gly Ile Ala Thr Ala Ile Met Asn Ser Asp Cys
                245                 250                 255

Leu Val Phe Asp Thr Ser Ile Ala Gln Leu Phe Ala Glu Asn Gly Asn
            260                 265                 270

Leu Gly Ile Asn Val Thr Ile Ser Met Cys
            275                 280

<210> SEQ ID NO 30
<211> LENGTH: 1540
<212> TYPE: DNA
<213> ORGANISM: Homo sapiens

<400> SEQUENCE: 30
gtcccgtcgg tctcggcgcc gggaagaggc ggtggcgctg cccgcggtgg cggggggttgg      60 cgacggagcg cgttggtgcc aggaccgggg tccgaggcgc gctctccgcc cacagaaatg     120
agccgtcaga ctgctacagc attacctacc ggtacctcga agtgtccacc atcccagagg     180
gtgcctgccc tgactggcac aactgcatcc aacaatgact tggcgagtct ttttgagtgt     240
ccagtctgct ttgactatgt gttaccgccc attcttcaat gtcagagtgg ccatcttgtt     300
tgtagcaact gtcgcccaaa gctcacatgt tgtccaactt gccggggccc tttgggatcc     360
attcgcaact tggctatgga gaaagtggct aattcagtac ttttcccctg taaatatgcg     420
tcttctggat gtgaaataac tctgccacac acagaaaaag cagaccatga agagctctgt     480
gagtttaggc cttattcctg tccgtgccct ggtgcttcct gtaaatggca aggctctctg     540
gatgctgtaa tgccccatct gatgcatcag cataagtcca ttacaaccct acaggagag      600 gatatagttt tccttgctac agacattaat cttcctggtg ctgttgactg ggtgatgatg     660
cagtcctgtt ttggctttca cttcatgtta gtcttagaga acaggaaaa atacgatggt      720 caccagcagt tcttcgcaat cgtacagctg ataggaacac gcaagcaagc tgaaaatttt     780
gcttaccgac ttgagctaaa tggtcatagg cgacgattga cttgggaagc gactcctcga     840
tctattcatg aaggaattgc aacagccatt atgaatagcg actgtctagt ctttgacacc     900
agcattgcac agcttttttgc agaaaatggc aatttaggca tcaatgtaac tatttccatg     960
tgttgaaatg gcaatcaaac attttctggc cagtgtttaa aacttcagtt tcacagaaaa    1020
taaggcaccc atctgtctgc caacctaaaa ctctttcggt aggtggaagc tagacacatg    1080
aaggtaaata aaaagaaagg ctgttaaata caggaaacag ttgcatgtag taacactaat    1140
atatttaaaa ataagtcaac agtaaaccac tgaaaaaata tatgtatata cacccaagat    1200
gggcatcttt tgtattaaga aaggaagcat tgtaaaataa ttctgagttt tgtgtttgtt    1260
gtagattgat tgtattgttg aaaaagtttg ttttttgcgtg ggagtgtgtg cctgcgtggg    1320
tgtgtgcgtg tttgggtttt tttccttttaa ctgacaagcc atcttgagtg gtcatgggcc    1380
actgcttttc cctttgtgag tcaatacata gtgctgctgt gtgctttttt tgtgtgtatt    1440 tgctaattttt tattaatttt agttttttcat taaataaatt tgacttttct gtaaaaaaaa    1500 aaaaaaaaa aaaaaaaaa aaaaaaaaa aaaaaaaaa                              1540

<210> SEQ ID NO 31
<211> LENGTH: 317

```
<212> TYPE: PRT
<213> ORGANISM: Homo sapiens

<400> SEQUENCE: 31

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

Leu Gln Glu Ile Arg Leu Glu Pro Gln Glu Val Pro Arg Gly Ser Glu
        50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
                100                 105                 110

Thr Pro Leu His Leu Ala Val Ile Thr Asn Gln Pro Glu Ile Ala Glu
            115                 120                 125

Ala Leu Leu Gly Ala Gly Cys Asp Pro Glu Leu Arg Asp Phe Arg Gly
        130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
                180                 185                 190

His Gly Tyr Leu Gly Ile Val Glu Leu Leu Val Ser Leu Gly Ala Asp
            195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315

<210> SEQ ID NO 32
<211> LENGTH: 9
<212> TYPE: PRT
<213> ORGANISM: Artificial Sequence
<220> FEATURE:
<223> OTHER INFORMATION: amino acid sequence of Human influenza
      hemagglutinin

<400> SEQUENCE: 32

Tyr Pro Tyr Asp Val Pro As

<210> SEQ ID NO 33
<211> LENGTH: 10
<212> TYPE: PRT
<213> ORGANISM: Artificial Sequence
<220> FEATURE:
<223> OTHER INFORMATION: amino acid sequence of Myc

<400> SEQUENCE: 33

Glu Gln Lys Leu Ile Ser Glu Glu Asp Leu
1               5                   10

<210> SEQ ID NO 34
<211> LENGTH: 10
<212> TYPE: DNA
<213> ORGANISM: Artificial Sequence
<220> FEATURE:
<223> OTHER INFORMATION: amino acid sequence of NF-kappaB specific DNA
      binding site

<400> SEQUENCE: 34
gggaatttcc                                                              10

<210> SEQ ID NO 35
<211> LENGTH: 54
<212> TYPE: PRT
<213> ORGANISM: Artificial Sequence
<220> FEATURE:
<223> OTHER INFORMATION: 112-165 aa fragment of Nkx3.2

<400> SEQUENCE: 35

Gly Ala Ser Gly Ala Gly Leu Ala Gly Gly Ser Leu Ser Leu Gly Gln
1               5                   10                  15

Pro Val Cys Glu Leu Ala Ala Ser Lys Asp Leu Glu Glu Glu Ala Ala
                20                  25                  30

Gly Arg Ser Asp Ser Glu Met Ser Ala Ser Val Ser Gly Asp Arg Ser
            35                  40                  45

Pro Arg Thr Glu Asp Asp
        50

<210> SEQ ID NO 36
<211> LENGTH: 162
<212> TYPE: DNA
<213> ORGANISM: Artificial Sequence
<220> FEATURE:
<223> OTHER INFORMATION: nucleotide sequence encoding 112-165 aa
      fragment of Nkx3.2

<400> SEQUENCE: 36
ggggccagcg gggccggcct tgcgggggga tccttgagcc tcggccagcc ggtctgtgag      60
ctggccgctt ccaaagacct agaggaggaa gccgcgggcc ggagcgacag cgagatgtcc     120
gccagcgtct caggcgaccg cagcccaagg accgaggacg ac                        162

<210> SEQ ID NO 37
<211> LENGTH: 164
<212> TYPE: PRT
<213> ORGANISM: Artificial Sequence
<220> FEATURE:
<223> OTHER INFORMATION: 154-317 aa fragment of Nkx3.2

<400> SEQUENCE: 37

Val Ser Gly Asp Arg Ser Pro Arg Thr Glu Asp Asp Gly Val Gly Pro
1               5                   10                  15

Arg Gly Ala His Val Ser Ala Leu Cys Ser Gly Ala Gly Gly Gly Gly

```
            20                  25                  30
Gly Ser Gly Pro Ala Gly Val Ala Glu Glu Glu Glu Pro Ala Ala
        35                  40                  45

Pro Lys Pro Arg Lys Lys Arg Ser Arg Ala Ala Phe Ser His Ala Gln
    50                  55                  60

Val Phe Glu Leu Glu Arg Arg Phe Asn His Gln Arg Tyr Leu Ser Gly
65                  70                  75                  80

Pro Glu Arg Ala Asp Leu Ala Ala Ser Leu Lys Leu Thr Glu Thr Gln
                85                  90                  95

Val Lys Ile Trp Phe Gln Asn Arg Arg Tyr Lys Thr Lys Arg Arg Gln
            100                 105                 110

Met Ala Ala Asp Leu Leu Ala Ser Ala Pro Ala Ala Lys Lys Val Ala
                115                 120                 125

Val Lys Val Leu Val Arg Asp Asp Gln Arg Gln Tyr Leu Pro Gly Glu
            130                 135                 140

Val Leu Arg Pro Pro Ser Leu Leu Pro Leu Gln Pro Ser Tyr Tyr Tyr
145                 150                 155                 160

Pro Tyr Tyr Cys
```

```
<210> SEQ ID NO 38
<211> LENGTH: 492
<212> TYPE: DNA
<213> ORGANISM: Artificial Sequence
<220> FEATURE:
<223> OTHER INFORMATION: nucleotide sequence encoding 154-317 aa
      fragment of Nkx3.2

<400> SEQUENCE: 38
gtctcaggcg accgcagccc aaggaccgag gacgacggtg ttggccccag aggtgcacac       60
gtgtccgcgc tgtgcagcgg ggccggcggc ggggcggca gcgggccggc aggcgtcgcg      120
gaggaggagg aggagccggc ggcgcccaag ccacgcaaga gcgctcgcg ggccgctttc      180 tcccacgcgc aggtcttcga gctggagcgc cgctttaacc accagcgcta cctgtccggg      240
cccgagcgcg cagacctggc cgcgtcgctg aagctcaccg agacgcaggt gaaaatctgg      300
ttccagaacc gtcgctacaa gacaaagcgc cggcagatgg cagccgacct gctggcctcg      360
gcgcccgccg ccaagaaggt ggccgtaaag gtgctggtgc gcgacgacca gagacaatac      420
ctgcccggcg aagtgctgcg gccacccctcg cttctgccac tgcagccctc ctactattac      480
ccgtactact gc                                                          492
```

```
<210> SEQ ID NO 39
<211> LENGTH: 42
<212> TYPE: PRT
<213> ORGANISM: Artificial Sequence
<220> FEATURE:
<223> OTHER INFORMATION: 112-153 aa fragment of Nkx3.2

<400> SEQUENCE: 39

Gly Ala Ser Gly Ala Gly Leu Ala Gly Gly Ser Leu Ser Leu Gly Gln
1               5                   10                  15

Pro Val Cys Glu Leu Ala Ala Ser Lys Asp Leu Glu Glu Glu Ala Ala
            20                  25                  30

Gly Arg Ser Asp Ser Glu Met Ser Ala Ser
        35                  40
```

```
<210> SEQ ID NO 40
<211> LENGTH: 126
```

```
<212> TYPE: DNA
<213> ORGANISM: Artificial Sequence
<220> FEATURE:
<223> OTHER INFORMATION: nucleotide sequence encoding 112-153 aa
      fragment of Nkx3.2

<400> SEQUENCE: 40
ggggccagcg gggccggcct tgcggggga tccttgagcc tcggccagcc ggtctgtgag      60
ctggccgctt ccaaagacct agaggaggaa gccgcgggcc ggagcgacag cgagatgtcc    120
gccagc                                                               126

<210> SEQ ID NO 41
<211> LENGTH: 16
<212> TYPE: PRT
<213> ORGANISM: Artificial Sequence
<220> FEATURE:
<223> OTHER INFORMATION: 318-333 aa fragment of Nkx3.2

<400> SEQUENCE: 41

Leu Pro Gly Trp Ala Leu Ser Thr Cys Ala Ala Ala Ala Gly Thr Gln
1               5                   10                  15

<210> SEQ ID NO 42
<211> LENGTH: 48
<212> TYPE: DNA
<213> ORGANISM: Artificial Sequence
<220> FEATURE:
<223> OTHER INFORMATION: nucleotide sequence encoding 318-333 aa
      fragment of Nkx3.2

<400> SEQUENCE: 42
ctcccaggct gggcgctctc cacctgcgca gctgccgcag gcacccag                  48
```